United States Patent [19]

Goeddel

[11] 4,414,150
[45] Nov. 8, 1983

[54] HYBRID HUMAN LEUKOCYTE INTERFERONS

[75] Inventor: David V. Goeddel, Burlingame, Calif.

[73] Assignee: Genentech, Inc., South San Francisco, Calif.

[21] Appl. No.: 237,388

[22] Filed: Feb. 23, 1981

Related U.S. Application Data

[63] Continuation-in-part of Ser. No. 205,579, Nov. 10, 1980.

[51] Int. Cl.$^3$ .................. C07C 103/52; C07G 7/00; C12P 21/00; C12P 21/02; C12N 15/00; C12N 1/00; A61K 45/02
[52] U.S. Cl. .................. 260/112.5 R; 260/112 R; 435/68; 435/70; 435/172; 435/317; 435/811; 424/85
[58] Field of Search .................. 424/85; 435/68, 70, 435/172, 317, 811; 260/112 R, 112.5 R

[56] References Cited

U.S. PATENT DOCUMENTS 4,262,090 4/1981 Colby et al. .................. 435/172

OTHER PUBLICATIONS

Derynck et al., Nature 285, 542 (1980).
Nagata et al., Nature 284, 316 (1980).
Taniguchi et al., Proc. Japan. Acad. Sci. Ser B 55, 464 (1979).
Research Disclosure, Jul. 1979, pp. 351–352.
Nienhuis et al., New Eng. J. Med. 297, 1318 (1977).
Miozzari et al., Nature 277, 486 (1979).
Itakura et al., Science 196, 1056 (1977).

Primary Examiner—Alvin E. Tanenholtz
Assistant Examiner—James Martinell
Attorney, Agent, or Firm—Jon S. Saxe; George M. Gould

[57] ABSTRACT

Disclosed herein are methods and means of microbially preparing novel human hybrid leukocyte interferons, useful in the treatment of viral and neoplastic diseases, by DNA recombination of parental interferon genes, taking advantage of common restriction endonuclease cleavage sites therein and in carrier expression plasmids.

7 Claims, 8 Drawing Figures

```
              -60                 -40                 -20                 +1                  20                  40
LeIF A  TGAGCCTAAACCTTAGGCTCACCCATTTCAACCAGTCTAGCAGCATCTGCAACATCTACAATGGCCTTGACCTTTGCTTTACTGGTGCCCTCCTGGTGC
LeIF B                         TACTAGCTCAGCAGCATCGCAACATCTACAATGCCCTTGACTTTTTATTTAATGGTGGCCCTAGTGGTGC
LeIF C            CAAGGTTATCCATCTCAAGTAGCCTAGCAATATTTGCAACATCCCAATGGCCCTGTCCTTTTCTTTACTTATGGCCGTGCTGGTGC
LeIF D            CAAGGTTCAGAGTCACCCATCTCAGCAAGCCCAGAAGTATCTGCAATATCTACGATGGCCTCGCCCTTTGCTTTACTGATGGTCCTGGTGGTGC
LeIF E
LeIF F                                                            ACATCCCAATGGCCCTGTCCTTTTCTTTACTGATGGCCGTGCTGGTGC
LeIF G
LeIF H       CCAAGGTTCAGTGTTACCCCTCATCAACCAGCCCAGCAGCATCTTCGGGATTCCCAATGGCATTGCCCTTTGCTTTAATGATGGCCCTGGTGGTGC 60                  80                  100                 120                 140
LeIF A  TCAGCTGCAAGTCAAGCTGCTCTGTGGGCTGTGATCTGCCTCAAACCCACAGCCTGGGTAGCAGGAGGACCTTGATGCTCCTGGCACAGATGAGGAAAAT
LeIF B  TCAGCTACAAGTCATTCAGCTCTCTGGGCTGTGATCTGCCTCAGACTCACAGCCTGGGTAACAGGAGGGCCTTGATACTCCTGGCACAAATGCGAAGAAT
LeIF C  TCAGCTACAAATCCATCTGTTCTCTGGGCTGTGATCTGCCTCAGACCCACAGCCTGGGTAATAGGAGGGCCTTGATACTCCTGGGACAAATGGGAAGAAT
LeIF D  TCAGCTGCAAGTCAAGCTGCTCTCTGGGCTGTGATCTCCCTGAGACCCACAGCCTGGATAACAGGAGGACCTTGATGCTCCTGGCACAAATGAGCAGAAT
LeIF E          CTGCCTCTGGGCTGTGATCTGCCTCAGGCCCACAGCCTGGGTAACAGGAGGGCCTTCATACTCCTGACACAAATGAGGAGAAT
LeIF F  TCAGCTACAAATCCATCTGTTCTCTGGGCTGTGATCTGCCTCAGACCCACAGCCTGGGTAATAGGAGGGCCTTGATACTCCTGGCACAAATGGGAAGAAT
LeIF G
LeIF H  TCAGCTGCAAGTCAAGCTGCTCTCTGGGCTGTAATCTGTCTCAAACCCACAGCCTGAATAACAGGAGGACTTTGATGCTCATGGCACAAATGAGGAGAAT 160                 180                 200                 220                 240
LeIF A  CTCTCTTTTCTCCTGCTTGAAGGACAGACATGACTTTGGATTTCCC CAGGAGGAGTTT     GGCAACCAGTTCCAAAAGGCTGAAACCATCCCTGTCCT
LeIF B  CTCTCCTTTCTCCTGCCTGAAGGACAGACATGACTTTGAATTCCCC CAGGAGGAGTTTGATGATAAACAGTTCCAGAAGGCTCAAGCCATCTCTGTCCT
LeIF C  CTCTCCTTTCTCCTGCCTGAAGGACAGACATGATTTCCGAATCCCC CAGGAGGAGTTTCATGGCAACCAGTTCCAGAAGGCTCAAGCCATCTCTGTCCT
LeIF D  CTCTCCTTCCTCCTGTCTGATGGACAGACATGACTTTGGATTTCCC CAGGAGGAGTTTGATGGCAACCAGTTCCAGAAGGCTCCAGCCATCTCTGTCCT
LeIF E  CTCTCCTTTTCTTACCTGAAGGACAGACATGACTTTGATTTTCCATCATCAGGTGTTTCATGGCAACCACTTCCAGAAGGTTCAAGCTATCTTCCTTTT
LeIF F  CTCTCCTTTCTCCTGCCTGAAGGACAGACATGACTTTGGATTCCCC CAAGAGGAGTTTGATGGCAACCAGTTCCAGAAGGCTCAAGCCATCTCTGTCCT
LeIF G              CATGACTTTGGATTTCCT CAGGAGGAGTTTGATGGCAACCAGTTCCAGAAGGCTCAAGCCATCTCTGTCCT
LeIF H  CTCTCCTTTCTCCTGCCTGAAGGACAGACATGACTTTGAATTTCCC CAGGAGGAATTTGATGGCAACCAGTTCCAGAAAGCTCAAGCCATCTCTGTCCT 260                 280                 300                 320                 340
LeIF A  CCATGAGATGATCCAGCAGATCTTCAATCTCTTCAGCACAAAGGACTCATCTGCTGCTTGGGATGAGACCCTCCTAGACAAATTCTACACTGAACTCTAC
LeIF B  CCATGAGATGATCCAGCAGACCTTCAACCTCTTCAGCACAAAGGACTCATCTGCTGCTTGGATTGAGACGACCCTTCTAGATGAATTCTACATCGAACTGAC
LeIF C  CCATGAGATGATCCAGCAGACCTTCAATCTCTTCAGCACAGAGGACTCATCTGCTGCTTGGGAACAGAGCCTCCTAGAAAAATTTTCCACTGAACTTTAC
LeIF D  CCATGAGCTGATCCAGCAGATCTTCAACCTCTTTACCACAAAAGATTCATCTGCTGCTTGGGATGAGGACCTCCTAGACAAATCTTGCACCGAACTCTAC
LeIF E  CCATGAGATGATGCAGCAGACCTTCAACCTCTTCAGCACAAAGGACTCATCTGATACTTGGGATGAGACCCTTTTAGACAAATCCTACACTGAACTTTAC
LeIF F  CCATGAGATGATCCAGCAGACCTTCAATCTCTTCAGCACAAAGGACTCATCTGCTACTTGGGAACAGAGCCTCCTAGAAAAATTTCCACTGAACTTAAC
LeIF G  CCATGAGATGATCCAGCAGACCTTCAATCTCTTCAGCACAAAGGACTCATCTGCTACTTGGGATGAGACACTTCTAGACAAATTCTACACTGAACTTTAC
LeIF H  CCATGAGATGATGCAGCAGACCTTCAATCTCTTCAGCACAAAGAACTCATCTGCTGCTTGGGATGAGACCCTCCTAGAAAAATTCTACATTGAACTTTTC 360                 380                 400                 420                 440
LeIF A  CAGCAGCTGAATGACCTGGAAGCCTGTGTGATACAGGGGGTGGGGGTGACAGAGACTCCCCTGATGAAGGAGGACTCCATTCTGGCTGTGAGGAAATACT
LeIF B  CAGCAGCTGAATGACCTGGAAGTCCTGTGTGATCAGGAAGTGGGGGTGATAGAGTCTCCCCTGATGTACGAGGACTCCATCCTGGCTGTGAGGAAATACT
LeIF C  CAGCAACTGAATGACCTGGAAGCATGTGTGATACAGGAGGTTGGGGTGGAAGAGACTCCCCCTGATGAATGAGGACTCCATCCTGGCTGTGAGGAAATACT
LeIF D  CAGCAGCTGAATGACTTGGAAGCCTGTGTGATGCAGGAAGGAGAGGGTGGGAGAAACTCCCCTGATGAATGTGGACTCCATCCTTGGCTGTGAAGAAATACT
LeIF E  CAGCAGCTGAATGACCTGGAAGCCTGTGTGATGTAGAAGGTTGGAGTGGAAGAGACTCCCCTGAGGAATGTGGACTCCATCCTGGCTGTGAGGAAATACT
LeIF F  CAGCAGCTGAACATGGAAAGCCTGCGTGATACAGGAGGTTGGGGTGGAAGAGACTCCCCTGATGAATGTGGACTCCATCCTGGCTGTGAAGAAATACT
LeIF G  CAGCAGCTGAATGACCTGGAAGCCTGTATGATGCAGGAGGTTGGAGTGGAAGACACTCCTCTGATGAATGTGGACTCTATCCTGACTGTGAAGAAATACT
LeIF H  CAGCAAATGAATGACCTGGAAGCCTGTGTGATACAGGAGGTTGGGGTGGAAGACACTCCCCTGATGAATGAGGACTCCATCCTGGCTGTGAAGAAATACT 460                 480                 500                 520                 540
LeIF A  TCCAAAGAATCACTCTCTATCTGAAAGAGAAGAAATACAGCCCTTGTGCCTGGGAGGTTGTCAGAGCAGAAATCATGAGATCTTTTTCTTTGTCAACAAA
LeIF B  TCCAAAGAATCACTCTATATCTGACAGAGAAGAAATACAGCTCTTGTGCCTGGGAGGTTGTCAGAGCAGAAATCATGAGATCGCTTCTCTTTATCAATCAA
LeIF C  TCCAAAGAATCACTCTTTATCTAATAGAGAGGAAATACAGCCCTTGTGCCTGGGAGGTTGTCAGAGCAGAAATCATGAGATCCCCTCTCTGTTTTCAACAAA
LeIF D  TCCGAAGAATCACTCTCTATCTGACAGAGAAGAAATACAGCCCCTTGTGCCTGGGAGGTTGTCAGAGCAGAAATCATGAGATCCCTCTCCTTTATCAACAAA
LeIF E  TTCAAAGACTCACTCTTTATCTGACAAAGAAGAAGTATAGCCCTTGTTCCTGGGAGGTTGTCAGAGCAGAAATCATGAGATCCTTCTCTTTTATGAACGAA
LeIF F  TCCAAAGAATCACTCTTTATCTGACAGAGAAGAAATACAGCCCCTTGTGCCTGGGAGGTTGTCAGAGCAGAAATCATGAGATCCCTTCTCTTTATCAAAAAT
LeIF G  TTCAAAGAATCACCCTCTATCTGACAGAGAAGAAATACAGCCCCTTGTGCATGGGAGGTTGTCAGAGCAGAAATCATGAGATCCTTCTCTTTATCAGCAAA
LeIF H  TCCAAAGAATCACTCTTTATCTGATGGAGAAGAAATACAGCCCCTTGTGCCTGGGAGGTTGTCAGAGCAGAAATCATGAGATCCTTCTCTTTTTTCAACAAA 560                 580                 600                 620                 640
LeIF A  CTTGCAAGAAAGTTTAAGAAGTAAGGAATGAAAACTGGTTCAACATGGAAATGATTTTCATTGATTCGTATGCCAGCTCACCTTTTTATGATCTGCCATT
LeIF B  CTTGCAAAAAAGATTGAAGAGTAAGGAATGAAGATGAGACCTGGTACAACAGCAGAAATGATTCTCATAGACTAATACAGCAGTCTACACTTGTATGCTC
LeIF C  CTTGCAAAAAAGATTAAGGAGGAAGGAATTGAAAACTGGTTCAACATGGCAATGATCCTGATTGACTAATACATTATCTCACACTTTCATGGAGTTCTTCCA
LeIF D  CTTGCAAGAAAGATTAAGGAGGAAGGAATAATATCTGGTCCAACATGAAAACAATTCTTATTGACTCATACACCAGGTCACGCTTTCATGAATTCGTGTCA
LeIF E  CTTGCAGGAAAGATTAAGGAGGAAGGAATGAAAACTGGTTCAACATGGAAATGAGAAACATTTCCATGATTAATACATCATCTCACACATTCATGAATTC
LeIF F  TTTTCAACAAAGATTAAGGAGGAAGGAATGAAAACCGTTTCAACATGGAAATGATCTGTATTGACTAATACAGCAGTCCACACTTCTATGACTTCTGCCAT
LeIF G  CTTGCAAGAAAGATTAAGGAGGAAGGAATGAAAACTGGTTCAACATGCAAATGATTCTCATTGACTAGTACACCATTTCACACTTCTTGAGTTCTGCCGT
LeIF H  CTTGCAAAAAAGATTAAGGAGGAAGGATTTGAAAACTGGTTCATCATGGAAATGATTCTCATTGACTAATACATCATCTCACACTTTCATGTTCTTCCATT 660                 680                 700                 720                 740
LeIF A  TCAAAGACTCATGTTTCTGCTATGACCATGACACGATTTAAATCTTTTCAAATGTTTTTAGGAGTATTAATCAACATTGTATTCAGCTCTTAAGGCACTA
LeIF B  TTTCAAAGACCCTTGTTTCTGCCAAAACCATGCTATCGAATTGAATCAAATGTGTCAAGTGTTTTCAGGAGTGTTAAGCAACATCCTGTTCAGCTGTATGG
LeIF C  TTTCAAAGACTCACTTCTATAACCACGACGCGTTGAATCAAAATTTTCAAATGTTTTCAGCAGTGTAAAGAAGTGTCGTGTATACCTGTGCAGGCACTAG
LeIF D  TTTCAAAGACTCTCACCCCTGCTATAACTATGACCATGCTGAAAACTGATTTATCTATTTAAAATATTTTATTTAACTATTTATGTAAATGGATTTAAATTATTTT
LeIF E  TGCCATTTCTCATTTTTGCTGTATATCCATGACATGAGTTGAATCAAAATTTTAAAATGTTTTCAGGAATGTTAAGCAGCATCATGTTCAGCTGTACAGGCA
LeIF F  TTGCAAACAAGATTAAGGAGGAAGGAATGAAAACCGTTTTCAACATGGAAATGATCTGTATTGACTAATACAGCAGTCCACACTTCTATGACTTCTGCCAT
LeIF G  TTCAAATATTTAATTTCTGCTATATCCATGACTTGAGTTGAATCAAAATTTTCAAACGTTTCACACGTGTTAAGCAACACTTCTTTAGCTCCACAGGGACA
LeIF H  TCAAAGACTCACTTCTATAACCACCACAAGTTGAATCAAAATTTTCCAAATGTTTTCAGGAGTGTTAAGAAGCATCGTGTTTACCTGTGCAGGCACTAGTC 760                 780                 800                 820                 840
LeIF A  GTCCCTTACAGAGGACCATGCTGACTGATCCATTATCTATTTAAATATTTTTAAAATATTATTTATTTAACTATTTATAAAACAACTTATTTTTGTTCAT
LeIF B  GCACTAGTCCCTTACAGATGACCATGCTGATGGATCTATTCATCTATTTATTTAAATCTTTATTTAGTTAACTACTATAGGGACTTAAATTAGTTTTGTT
LeIF C  TCCTTTACAGATGACCATTCTGATGTCTCTGTTCATCTTTTGTTTAAATATTTATTTAATTATTTTTAAAATTTATGTAATCATCATGAGTCGCTTTACAT
LeIF D  TGTTCATATAACGTCATGTGCACCTTTACACTGTGGTTAGTGTAATAAAACATGTTCCTTATATTTACTC-poly(A)
LeIF E  CTAGTTCCTTACGGATGCATCATGCTGATGGATCTGTTTATCTATTTGTCTAAATAATTATTTAACTATTTAAATAATATTTAAAATCTTCTTTTCATGTATC
LeIF F  CTAGTCCTTTACAGATGACCATGCTGATAGATCTAATTATCTATCTATTGAAATATTTATTTATTTATTAGATTTAAATTATTTTTGTCCATGTAATATT
LeIF G  AAATCTTTACAGATGATCATGCCAATCTATCTATTCATCTATTTATCTATCTGTCTGTCTTCTATCTAATTCTATATTTAAATATTTATTTATTTATAAGAT
LeIF H  CTTTACAGATGACCATTCTGATGTCTCCTTTCATCTATTTAAATATTTATTTTATTTAACTATTTTTATTATTTAAATTATTTTTTATGTAATATCA 860                 880                 900                 920                 940
LeIF A  ATTACGTCATGTGCACCTTTGCCACAGTGGTTAATGTAATAAAATATGTTCTTTGTATTTGGT-poly(A)
LeIF B  CATATTATATTATGTGAACTTTTACATTGTGAATTGTGTAACAAAAACATGTTCTTAATTTTATTATTTGCCATGTTTATTAAATTTTTACTATGAAAA
LeIF C  TGTCGTTAATGTAACAATATATGTTCTTCATATTTAGCCAATATATTAATTTCCTTTTTCATTAAATTTTTACTATAC-poly(A)
LeIF E  ATGTATTTTTTACTTTGTGGTTAATAACAACAGATGTTCTTTATATTTAGTGCTTTAACTTTTGCTTTTTTCATTAAATTTTTACTATGG-poly(A)
LeIF F  ATGTGTACTTTTACATTGTGTTATATCAAAATATGTTAATCTAATATTTAGTCAATATATATTTTCTTTTTATTAATTTTTACTATTAAAACTTCTTAT
LeIF G  TTAAATTATTTTAAACTTATGTTTGTTCAGGTAATATTACATCCACCTTACTTTGTGGCTAATATAATAAAATATGTTCTTTATGTTTTGTC-poly(A)
LeIF H  TGAGTACCCTTTACATTGTGGTTAATGTAACAAATATGTTCTTCATATTTAGCCAATATAATTAATTTCCTTTTTCATTAAATTTTTACTAT-poly(A)

960                 980                 1000
LeIF B  AATTCTTTATTTATTCTTTAAAATTGAACTCCAACCCATGAATTGTGCAAACTGATTAAAGAATGGATGGT-poly(A)
LeIF F  ATTATTTGGTTATTCTTTAATAAAGAAATTCCAAGCCC-poly(A)
```

HYBRID HUMAN LEUKOCYTE INTERFERONS

This is a continuation in part of application Ser. No. 205,579, filed Nov. 10, 1980.

FIELD OF THE INVENTION

This invention relates to the microbial production, via recombinant DNA technology, of hybrid leukocyte interferons for use in the treatment of viral and neoplastic diseases, and to the means and end products of such production.

CROSS REFERENCE TO RELATED APPLICATIONS

This application is in part related in subject matter to U.S. patent applications of David V. Goeddel and Sidney Pestka, Ser. No. 205,578, filed Nov. 10, 1980 and Ser. No. 184,909 filed Sept. 8, 1980. The disclosure of each of the foregoing, commonly owned, applications is incorporated herein by reference to illuminate the background of the invention and to provide additional detail relative to the practice thereof.

BACKGROUND OF THE INVENTION

Relatively homogeneous leukocyte interferons have been derived from normal or leukemic donors' leukocytes. These interferons are a family of proteins characterized by a potent ability to confer a virus-resistant state in their target cells. In addition, interferon can act to inhibit cell proliferation and modulate immune response. These properties have prompted the clinical use of interferon as a therapeutic agent for the treatment of viral infections and malignancies.

More recently, recombinant DNA technology has been employed to occasion the microbial production of a number of different leukocyte interferons whose amino acid sequences exhibit on the order of 70 percent homology, one relative to another, all as disclosed in the aforementioned U.S. patent applications of Goeddel an Pestka and in the manuscript of David V. Goeddel et al entitled "The Structures of Eight Distinct Cloned Human Leukocyte Interferon cDNAs", a copy of which is attached as Appendix A to the present application and incorporated herein. The manner in which genes encoding amino acid sequences of various leukocyte interferons designated, inter alia, LeIF A,B,C,D,F,G and H, respectively, are obtained from the cell line KG-1 described in Koeffler, H. P. and Golde, D. W. *Science* 200, 1153-1154 (1978) is disclosed in the aforementioned applications of Goeddel and Pestka. The cell line KG-1 has been deposited with the American type culture collection, ATCC Accession Number CRL 8031. Such genes, appropriately deployed in plasmidic vehicles for bacterial expression, may be employed to transform host bacteria, preferably *E. coli* K-12 strain 294, American type culture collection accession No. 31446.

BRIEF SUMMARY OF THE INVENTION

Nucleotide sequence studies of genes encoding the various leukocyte interferons reveals a degree of commonality amongst various of them with regard to the presence and location of cleavage sites recognized by particular restriction endonucleases. According to the present invention, advantage may be taken of this commonality to form, by DNA recombination, novel hydrid genes useful in the microbial production of hybrid leukocyte interferons which may be expected to exhibit in greater or lesser degree the antiviral and other properties of interferons encoded by the parental genes. In preferred embodiments of the invention, such hybrid leukocyte interferons may exhibit enhanced activity relative to those encoded by the parental genes.

The manner in which these and other objects and advantages of the invention are obtained will become further apparent from the detailed description which follows and from the accompanying drawings in which:

FIG. 2 depicts restriction endounuclease maps of eight types of LeIF cloned cDNAs (A through H). Plasmids containing the clones were constructed by the dC:dG tailing method, Goeddel, D.V. et al, *Nature* 287, 411-416 (1980). Therefore the cDNA inserts can be excised using Pst I, i.e., each end of each insert is a Pst I restriction endonuclease cleavage site. The lines at the end of each cDNA insert represent the flanking homopolymeric dC:dG tails. The positions of Pvu II, Eco RI and Bgl II restriction sites are indicated. Shaded regions of the Figure represent the coding sequences of mature LeIFs; the cross-hatched regions indicate signal peptide coding sequences; and the open regions show 3' and 5' noncoding sequences.

FIG. 3 is a comparision of the eight LeIF protein sequences predicted from the nucleotide sequences. The one letter abbreviations recommended by the IUPAC-IUB Commission on Biochemical Nomenclature are used: A, alanine; C, cysteine; D, aspartic acid; E, glutamic acid; F, phenylalanine; G, glycine; H, histidine; I, isoleucine; K, lysine; L, leucine; M, methionine; N, asparagine; P, proline; Q, glutamine; R, arginine; S, serine; T, threonene; V, valine; W, tryptophan; and Y, tyrosine. The numbers refer to amino acid position (S refers to signal piptide). The dash in the 165 amino acid LeIF A sequence at position 44 is introduced to align the LeIF A sequence with the 166 amino acid sequences of the other LeIFs. The LeIF E sequence was determined by ignoring the extra nucleotide (position 187 of FIG. 1) in its coding region. The asterisks indicate in-phase termination codons. Amino acids common to all LeIFs (excluding the pseudogene LeIF E) are also shown. The underlined residues are amino acids which are also present in human fibroblast interferon.

With reference to FIG. 1, nucleotides +1 to 69 correspond to S1 to S23 amino acids of FIG. 3. Codon TGT (nucleotides 70 to 72) of FIG. 1 corresponds to cysteine (C, amino acid 1) of FIG. 3. In FIG. 3, the Pvu II restriction endonuclease cleavage site occurs between the codons for amino acids 92 and 93 in LeIF A,B,D,F and G, i.e., between nucleotides 346 and 347, of FIG. 1.

FIG. 4 also indicates the relative position on the corresponding gene of Bgl II and Pvu II restriction endonuclease cleavage sites employed in forming preferred hybrid leukocyte genes of the invention.

DESCRIPTION OF THE PREFERRED EMBODIMENTS

The LeIF hybrids are prepared, in accordance with the present invention, by taking advantage of restriction endonuclease cleavage sites commonly located within the individual parental genes and each end thereof in conjunction with the same sites in carrier expression plasmids (vectors). For example, the large (~3900 bp) fragment of a Xba I to Pst I digest of the pLeIF A trp 25 expression plasmid can be ligated with Xba I to Pvu II and Pvu II to Pst I digest fragments of the various LeIF parental genes to provide expression plasmids operable to obtain the corresponding hybrod LeIF.

Each LeIF expression plasmid was constructed indipendently with digest fragments isolated from the plasmids pLeIF A trp 25, pLeIF B trp 7, pLeIF C trp 35, pLeIF D trp 11, pLeIF F trp 1, pLeIF G, and pLeIF H, whose construction and description are described in the aforementioned applications of Goeddel and Pestka, or pBR322 whose construction and description is described by Bolivar et al., Gene 2, 95 (1977). In certain of these plasmids, "trp" designates a tryptophan promoter-operator system most preferred for bacterial expression, as described in the copending, commonly owned U.S. patent application of Dennis G. Kleid et al., Ser. No. 133,296, filed Mar. 24, 1980.

The methods and materials employed in the following constructions were as in the aforementioned applications of Goeddel and Pestka. The following Tble 1 provides the details for particular constructions of hybrid LeIF plasmids hereof:

TABLE 1

| LeIF Hybrid | Total Amino Acids* | Expression Plasmid (Vector) | Front Portion Fragment | Amino Acids | Back Portion Fragment | Amino Acids | Resultant Expression Plasmid |
|---|---|---|---|---|---|---|---|
| AD | 165 | a | XbaI-PvuII of pLeIF A trp 25 (285 bp) | 1–91 | PvuII-PstI of pLeIF D trp 11 (~550 bp) | 93–166 | pLeIF AD trp (Pvu II) |
| DA | 166 | a | XbaI-PvuII of pLeIF D trp 11 (288 bp) | 1–92 | PvuII-PstI of pLeIF A trp 25 (~550 bp) | 92–165 | pLeIF DA trp (Pvu II) |
| AD | 165 | — | Bgl II-Pst I large fragment of pLeIF A trp 25 | 1–62 | Bgl II-Pst I of pLeIF D trp 11 (~600 bp) | 64–166 | pLeIF AD trp (Bgl II) |
| DA | 166 | — | Bgl II-Pst I large fragment pLeIF D trp 11 | 1–63 | Bgl II partial-Pst I of pLeIF A trp 25 (~700 bp) | 63–165 | pLeIF DA trp (Bgl II) |
| AB | 165 | a | XbaI-PvuII of LeIF A trp 25 (285 bp) | 1–91 | PvuII partial-PstI of pLeIF B trp 7 (~750 bp) | 93–166 | pLeIF AB trp (Pvu II) |
| AF | 165 | a | XbaI-PvuII of LeIF A trp 25 (285 bp) | 1–91 | Pvu II Pst I of pLeIF F trp 1 (~700 bp) | 93–166 | pLeIF AF trp (Pvu II) |
| AG | 165 | a | XbaI-PvuII of LeIF A trp 25 (285 bp) | 1–91 | PvuII-PstI of pLeIF G (~750 bp) | 93–166 | pLeIF AG trp (Pvu II) |
| BA | 166 | b | HindIII-PvuII of pLeIF B trp 7 (~630 bp) | 1–92 | PvuII-PstI of pLeIF A trp 25 (~550 bp) | 92–165 | pLeIF BA trp (Pvu II) |
| BD | 166 | b | HindIII-PvuII of pLeIF B trp 7 (~630 bp) | 1–92 | PvuII-PstI of pLeIF D trp 11 (~550 bp) | 93–166 | pLeIF BD trp (Pvu II) |
| BF | 166 | b | HindIII-PvuII of pLeIF B trp 7 (~630 bp) | 1–92 | PvuII-PstI of pLeIF F trp 1 (~700 bp) | 93–166 | pLeIF BF trp (Pvu II) |
| BG | 166 | b | HindIII-PvuII of pLeIF B trp 7 (~630 bp) | 1–92 | PvuII-PstI of pLeIF G (~750 bp) | 93–166 | pLeIF BG trp (Pvu II) |
| DB | 166 | a | XbaI-PvuII of pLeIF D trp 11 (288 bp) | 1–92 | PvuII partial-PstI of pLeIF B trp 7 (~750 bp) | 93–166 | pLeIF DB trp (Pvu II) |
| DF | 166 | a | XbaI-PvuII of pLeIF D trp 11 (288 bp) | 1–92 | PvuII-Pst I of pLeIF F trp 1 (~700 bp) | 93–166 | pLeIF DF trp (Pvu II) |
| DG | 166 | a | XbaI-PvuII of pLeIF D trp 11 (288 bp) | 1–92 | PvuII-PstI of pLeIF G (~750 bp) | 93–166 | pLeIF DG trp (Pvu II) |
| FA | 166 | a | XbaI-PvuII of pLeIF F trp 1 (288 bp) | 1–92 | PvuII-PstI of pLeIF A trp 25 (~550 bp) | 92–165 | pLeIF FA trp (Pvu II) |
| FB | 166 | a | XbaI-PvuII of pLeIF F trp 1 (288 bp) | 1–92 | PvuII partial-PstI of pLeIF B trp 7 (~750 bp) | 93–166 | pLeIF FB trp (Pvu II) |
| FD | 166 | a | XbaI-PvuII of pLeIF F trp 1 | 1–92 | PvuII-PstI from pLeIF D trp 11 | 93–166 | pLeIF FD trp (Pvu II) |

TABLE 1-continued

| LeIF Hybrid | Total Amino Acids* | Expression Plasmid (Vector) | Front Portion Fragment | Amino Acids | Back Portion Fragment | Amino Acids | Resultant Expression Plasmid |
|---|---|---|---|---|---|---|---|
| FG | 166 | a | (288 bp) XbaI-PvuII of pLeIF F trp 1 (288 bp) | 1-92 | (~550 bp) PvuII-PstI from pLeIF G (~750 bp) | 93-166 | pLeIF FG trp (Pvu II) |

*excluding N—terminal methionine
a large (~3900 bp) fragment of Xba I to Pst I digest of pLeIF A trp 25.
b large (~3600 bp) fragment of Hind III to Pst I digest of pBR322.

With further reference to Table I, the first four described hybrid LeIFs have been produced from two LeIF expression plasmids. A Bgl II site common to LeIF A and D cDNAs has been used to construct an expression plasmid pLeIF trp AD (Bgl II) which codes for the 63 amino terminal amino acids of LeIF A and the 102 carboxy terminal amino acids of LeIF D. The same site was utilized in the construction of an expression plasmid pLeIF trp DA (Bgl II) which codes for 64 amino terminal amino acids of LeIF D and 102 carboxy terminal amino acids of LeIF A. The Pvu II site has been used in the construction of two other hybrid interferon expression plasmids: 91 amino terminal amino acids of A with 74 carboxy terminal amino acids of D (LeIF tr AD (Pvu II)) and 92 amino terminal amino acids of LeIF D with 74 carboxy terminal amino acids of LeIF A (pLeIF trp DA (Pvu II)). In summary, for:

pLeIF AD trp (Pvu II): The large (~3900 bp) fragment of an XbA I and Pst I digest of pLeIF A trp 25 was ligated with a 286 bp Xba I-Pvu II fragment of pLeIF A trp 25 and an approximately 550 bp Pvu II-Pst I fragment of pLeIF D trp 11;

pLeIF DA trp (Pvu II): The large (~3900 bp) fragment of an Xba I and Pst I digest of pLeIF A trp 25 was ligated with a 288 bp Xba I-Pvu-II fragment of pLeIF D trp 11 and an approximately 550 bp Pvu II-Pst I fragment of pLeIF A trp 25;

pLeIF AD trp (Bgl II): The large fragment from a Bgl II, Pst I digest of pLeIF A trp 25 was ligated with a ~600 bp Bgl II-Pst I fragment from pLeIF D trp 11; and pLeIF DA trp (Bgl II): The large fragment from a Bgl II and Pst I digest of pLeIF D trp 11 was ligated to an approximately 700 bp fragment obtained by Pst I cleavage of pLeIF A trp 25 followed by partial Bgl II digestion.

In the fifth depicted hybrid:

pLeIF AB trp (Pvu II): The large (~3900 bp) fragment of an Xba I and Pst I digest of pLeIF A trp 25 was ligated with a 285 bp Xba I-Pvu II fragment of pLeIF A trp 25 and an approximately 750 bp Pvu II (partial)-Pst I fragment of pLeIF B trp 7.

In like manner, the other constructions depicted in Table I are so defined. As a further example, in the construction of a LeIF C and/or LeIF H portion containing hybrid, one can take advantage of common Bbv I sites occurring at about nucleotide 294 (i.e., GCTGC) of the gene sequences.

In like manner, plasmids suitable for the microbial expression of other novel hybrid leukocyte interferons may be formed by appropriate manipulation of double stranded DNA encoding all or portions of the amino acid sequences of natural occurring leudocyte interferons. Thus, a first double stranded DNA fragment is selected which encodes the amino terminal of a first, naturally occurring leukocyte interferon amino acid sequence and, proceeding therefrom in the 3' direction, a substantial portion of the amino acid sequence thereof. The fragment comprises a restriction endonuclease cleavage site positioned adjacent codons for amino acid "n" of the first leukocyte interferon, n amino acids constituting a substantial portion of the amino acid sequence of the first interferon. Cleavage with the restriction endonuclease yields a fragment comprising the amino terminal of the first interfereon and codons for approximately n amino acids. A second fragment comprising all or a portion of the codons for the amino acid sequence of a second, different leukocyte interferon is selected, the fragment comprising a cleavage site for an identical restriction endonuclease positioned adjacent codons for that amino acid of the second interferon whose amino acid number (proceeding from the amino terminal of the second interferon) is approximately 166-n. Cleavage of the second fragment with that restriction endonuclease yields a product complementary to the "n" terminal portion of the digestion product of the first fragment, such that the digestion product of the second can be ligated to that of the first, reforming the restriction endonuclease recognition site and reconstituting the codon for amino acid n of the first interferon, where lost in the initial digestion. The product of the restriction endonuclease digestion of the second fragment preferably proceeds from the end resulting from cleavage in the 3' direction through nucleotides encoding the carboxy terminal of the second leukocyte interferon.

Alternatively, hybrids containing substantial portions of the amino acid sequences of more than two naturally occurring leukocyte interferons may be formed, in which event, for example, the second fragment mentioned above is additionally chosen to contain a second restriction endonuclease site downstream from the first, the second site being identical to a similarly positioned site within a fragment encoding the carboxy terminal portion of a third leukocyte interferon, etc. In the example referred to, the products of successive restriction endonuclease operations may be triple-ligated to form a hybrid gene encoding the amino terminal portion of a first interferon, the mid-range amino acid sequence of the second and the carboxy terminal portion of the third, (or, in another variation of the first, where the first and third interferons are the same).

Preferably, the first fragment mentioned above is derived from an expression plasmid, i.e., one in which codons for the amino terminal portion of the first leukocyte interferon are preceded by an ATG or other translation initiation codon and a promoter or promoter-operator system. As a result, the end product of the manipulative operations described above will be a plasmid capable of expressing the polypeptide encoded by the hybrid gene in bacteria or other microbial organisms transformed with the plasmid. Other means of configuring the hybrid gene for microbial expression will be apparent to those skilled in the art.

Figure 1:
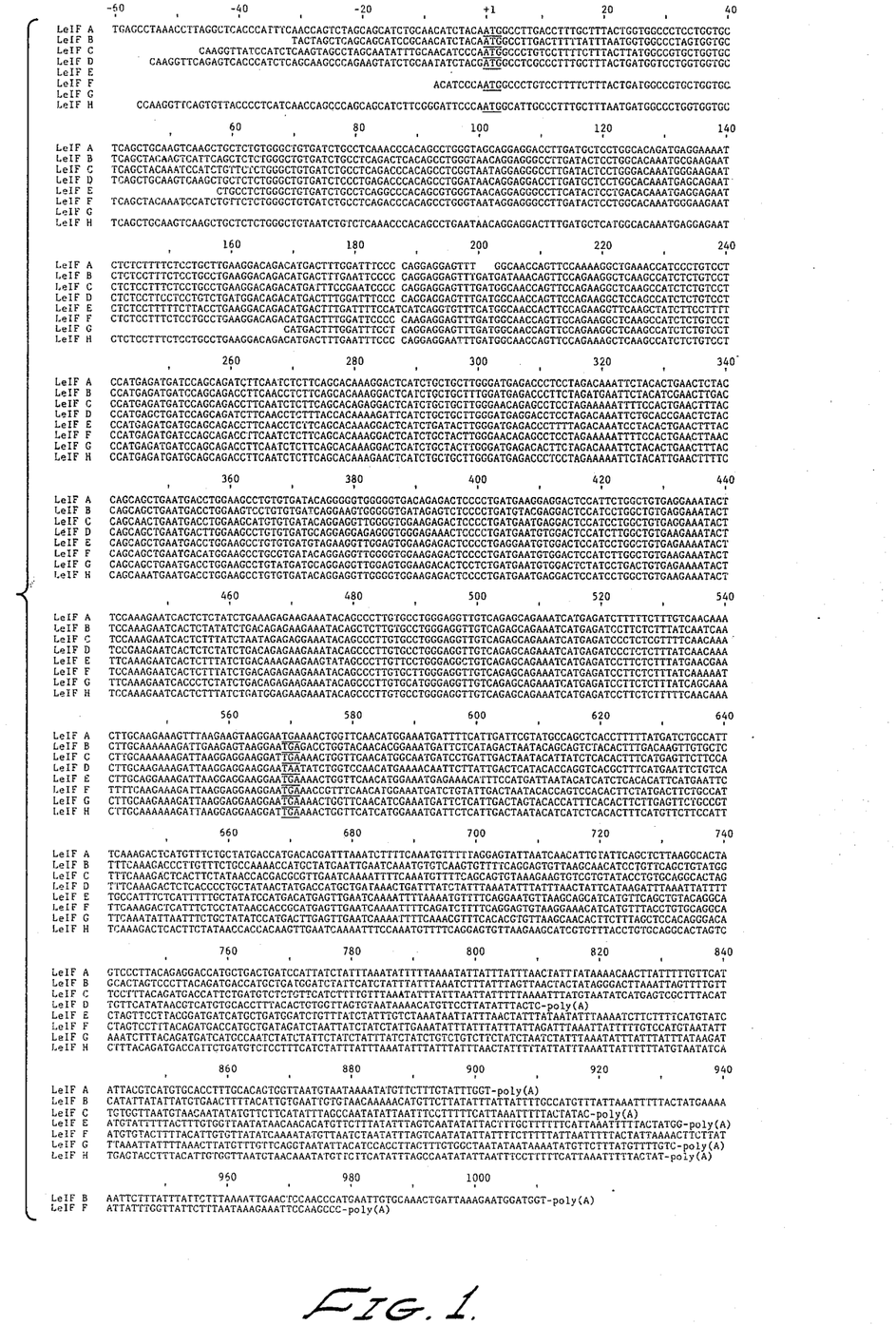
FIG. 1 depicts nucleotide sequences of the coding regions of 8 leukocyte interferon ("LeIF") complementary DNA ("cDNA") clones. Of these, one, correspondingly designated LeIF E, is an apparent "pseudogene" encoding no active leukocyte interferon while another, designated LeIF G, contains less than the full sequence for the corresponding interferon species. The ATG translational initiation codon and the termination triplet for each LeIF is underlined.
Figure 2:
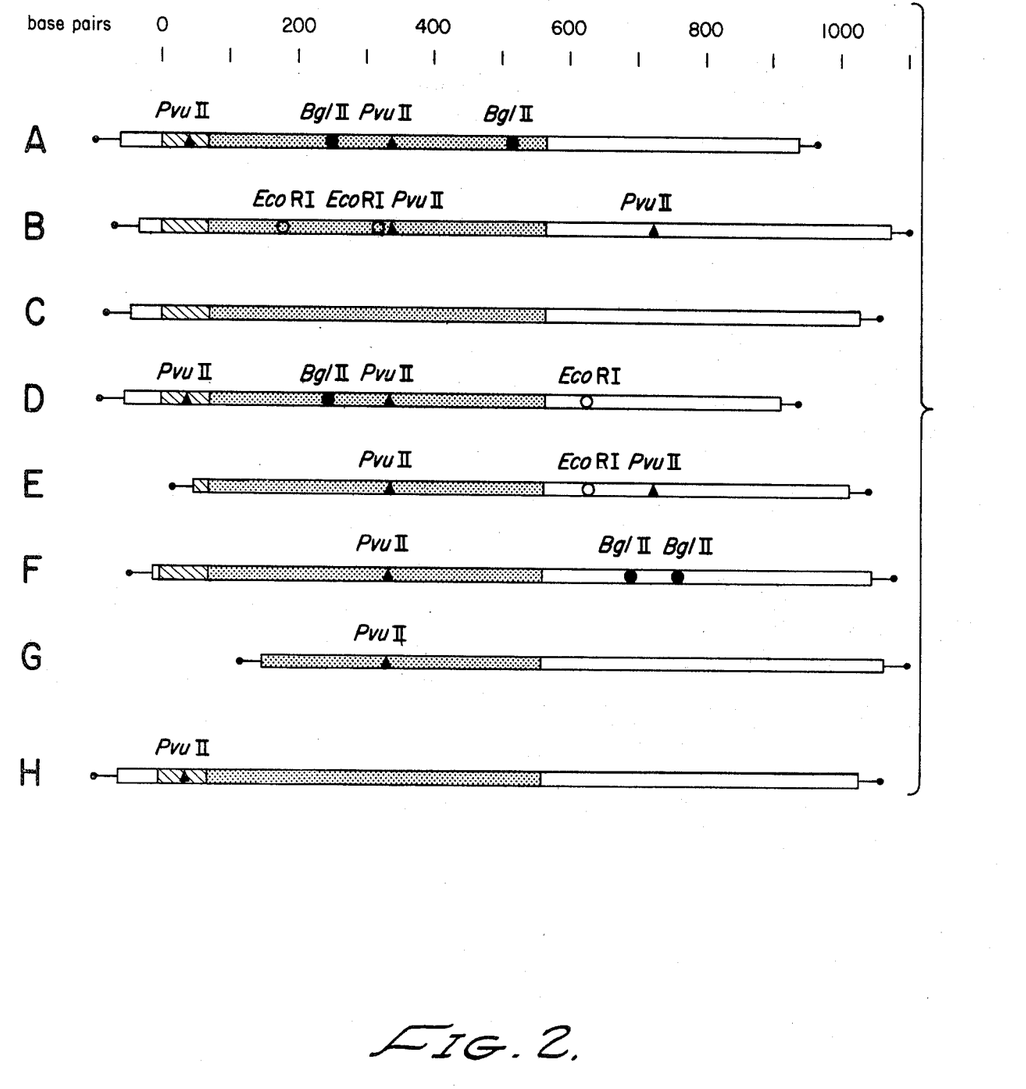
Figure 3:
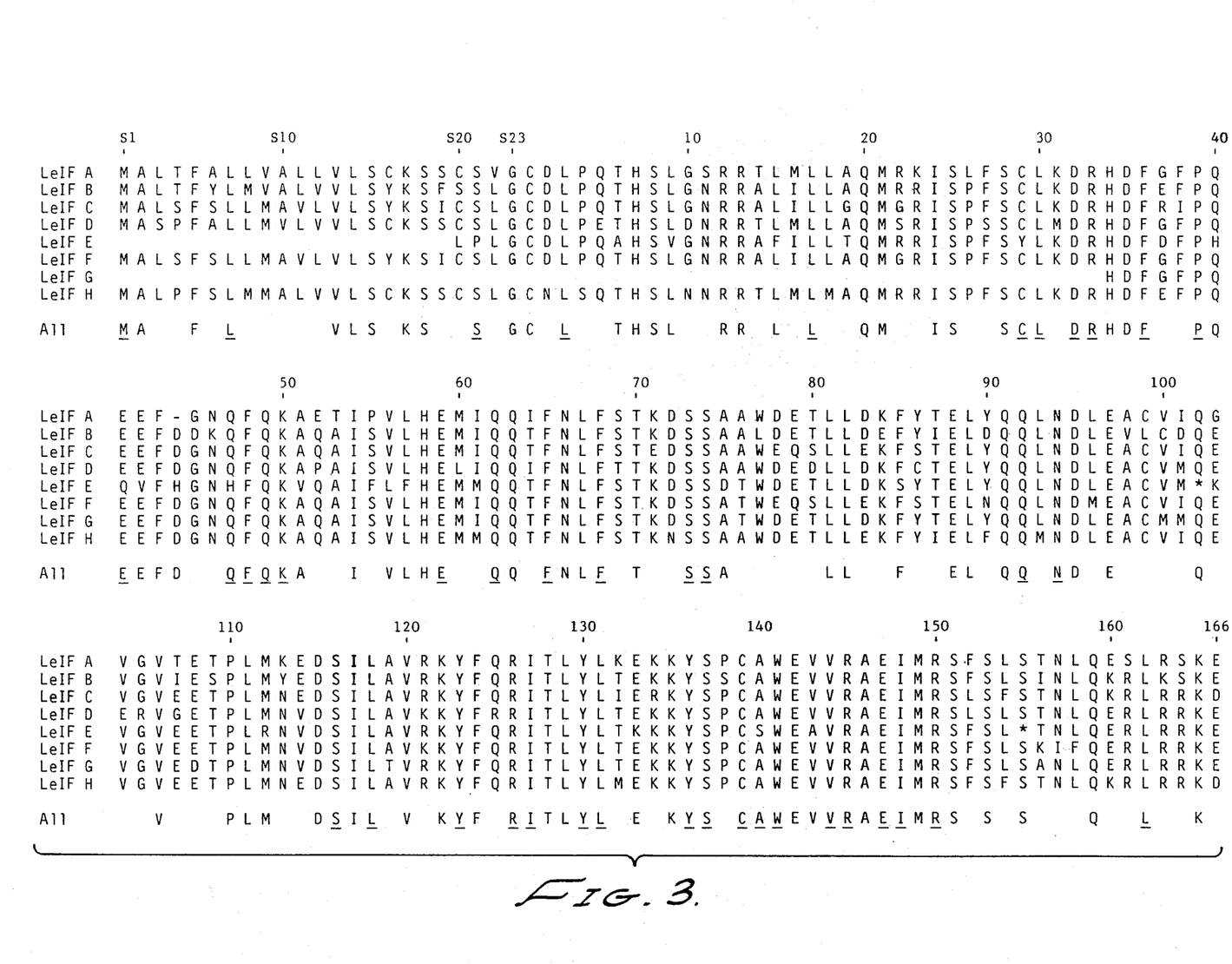

In preferred embodiments of the invention, the hybrid genes encode a novel leukocyte interferon amino acid sequence approximating 165-166 amino acids constituting a conjugate of substantial amino acid sequences drawn from two or more different leukocyte interferons selected from the group consisting of LeIF A, LeIF B, LeIF C, LeIF D, LeIF E, LeIF F, LeIF G, and LeIF H as depicted in FIG. 3. Most preferably, the novel leukocyte interferons encoded by the hybrid genes comprise the amino acids specified and positioned as indicated in the sequence "A11" of FIG. 3. The expression products of plasmids formed according to the invention may be tested for antiviral activity in conventional manner, as in the biological activity determinations next described.

DEMONSTRATION OF ANTIVIRAL ACTIVITY

E. coli K-12 strain 294 was conventionally transformed with, independently, the plasmids pLeIF trp A 25, pLeIF trp D, pLeIF trp A/D (Bgl II) and pLeIF trp D/A (Bgl II). The transformants were separately grown up in 5 ml cultures in L broth containing 5 mg/ml tetracycline to an $A_{550}$ of about 1.0, then diluted into one liter of M9 media containing 5 µg/ml tetracycline. Cells were harvested when $A_{550}$ reached 1.0 and cell pellets suspended in 10 ml of 15 percent sucrose, 50 mM tris-HCl (pH 8.0), 50 mM EDTA. 10 mg of lysozyme were added and, after 5 minutes at 0° C., cells were disrupted by sonication. The samples were centrifuged 10 minutes at 15,000 rpm in a Sorvall SM-24 rotor. Interferon activity in the supernatants was subjected to test for antiviral activity.

Further purification may be effected as in the aforementioned applications of Goeddel and Pestka.

The yields per liter of culture of these interferons, titrated on a human cell line (WISH) are shown in Table 2 from which it is apparent that LeIF-A/D activity is produced in greater amount than the other interferons. This difference could be due to greater intrinsic activity of the LeIF-A/D or to greater yield in terms of mg protein of this interferon. Because the genetic link-up was identical for all these interferons it seems most probable that LeIF-A/D essentially has greater activity than the other interferons.

TABLE 2

YIELD OF LEUKOCYTE INTERFERONS FROM SHAKING FLASK CULTURES OF E. COLI

| Type interferon | Activity Yield/Liter (Units on WISH)* |
|---|---|
| A | $8 \times 10^7$ |
| D | $5 \times 10^6$ |
| AD (Bgl II) | $2 \times 10^8$ |
| DA (Bgl II) | $1 \times 10^6$ |

*assayed by inhibition of cytopathic effect on WISH cells with VSV as challenge.

The potency of the various interferons in a range of mammalian cell lines was determined (human, WISH; African green monkey, VERO; hamster fibroblast, BHK; rabbit kidney cells, RK-13; mouse L-929; and bovine kidney, MDBK cells). In order to compare the relative activity of the interferons their activity on various cells was calculated relative to their activity on WISH cells taken as 100. The results in Table 3 show that LeIF-A/D has very high activity in VERO and L-929 cells whereas LeIF-D/A has low activity in these cell lines. These results indicate that the combination of the N-terminal portion of LeIF-A and the C-terminal portion of LeIF-D within one molecule (LeIF-A/D) confers to the hybrid protein particular potency which is manifest in several mammalian species. Moreover, these properties are not simply the summation of the properties of the parent interferons. This is clearly seen in the case of activity on L-929 cells (Table 3) in which case neither a mixture of LeIF-A and LeIF-D nor the other hybrid, LeIF-D/A, has significant activity.

TABLE 3

TITRATION OF VARIOUS LEUKOCYTE INTERFERONS IN CELL LINES FROM VARIOUS MAMMALIAN SPECIES

| Cell line | Leukocyte interferons* | | | | | |
|---|---|---|---|---|---|---|
| | A | D | A/D | D/A | A + D | Buffy-coat |
| WISH | 100 | 100 | 100 | 100 | 100 | 100 |
| VERO | 250 | 75 | 1,670 | 20 | 200 | 200 |
| BHK | 400 | 200 | 833 | 2,000 | 400 | 20 |
| RK-13 | 12 | 500 | 6 | N.D. | N.D. | 120 |
| L-929 | 150 | 5 | 3,300 | 2 | 10 | 0.1 |

*Interferons tested against VSV infection of the different cell lines.
Activities expressed as percentage of activity observed in WISH cells.

Figure 5:
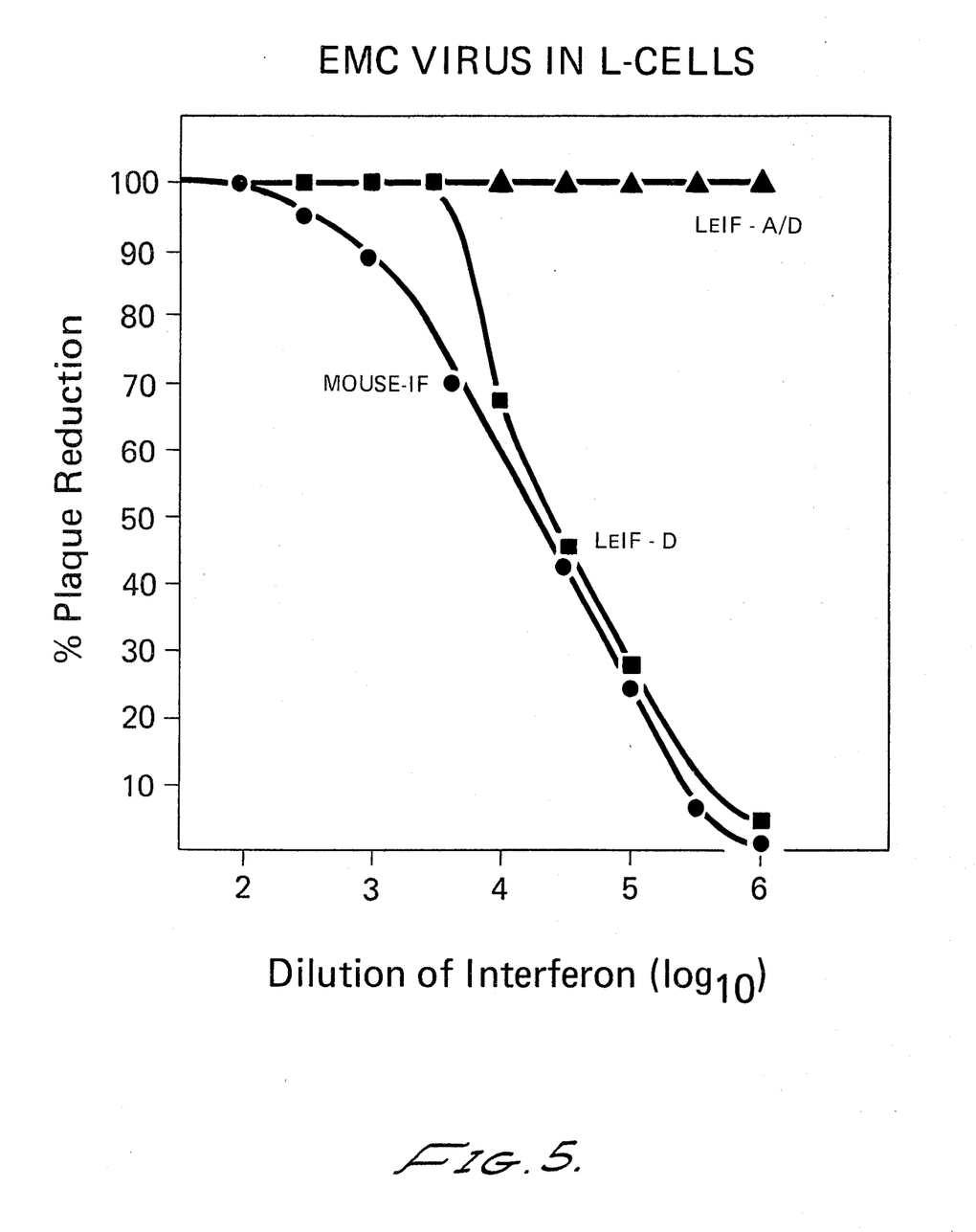
FIGS. 5 and 6 illustrate the results of comparative testing of a preferred hybrid leukocyte interferon of the invention ("LeIF-A/D") for activity against encephalomyocarditis virus ("EMC") and vesicular stomatitis virus ("VSV"), respectively, in mouse cells.
Figure 6:
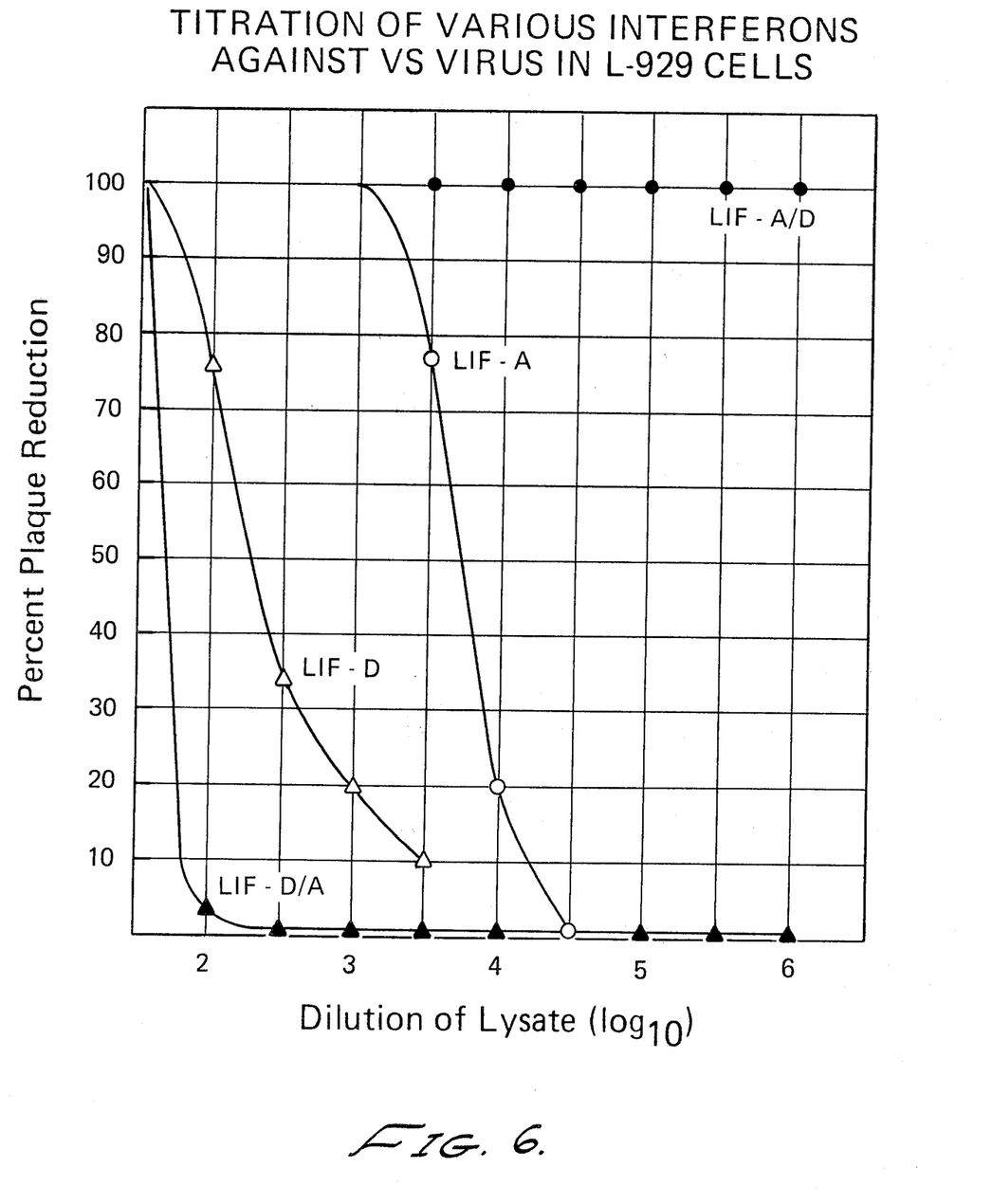
Figure 7:
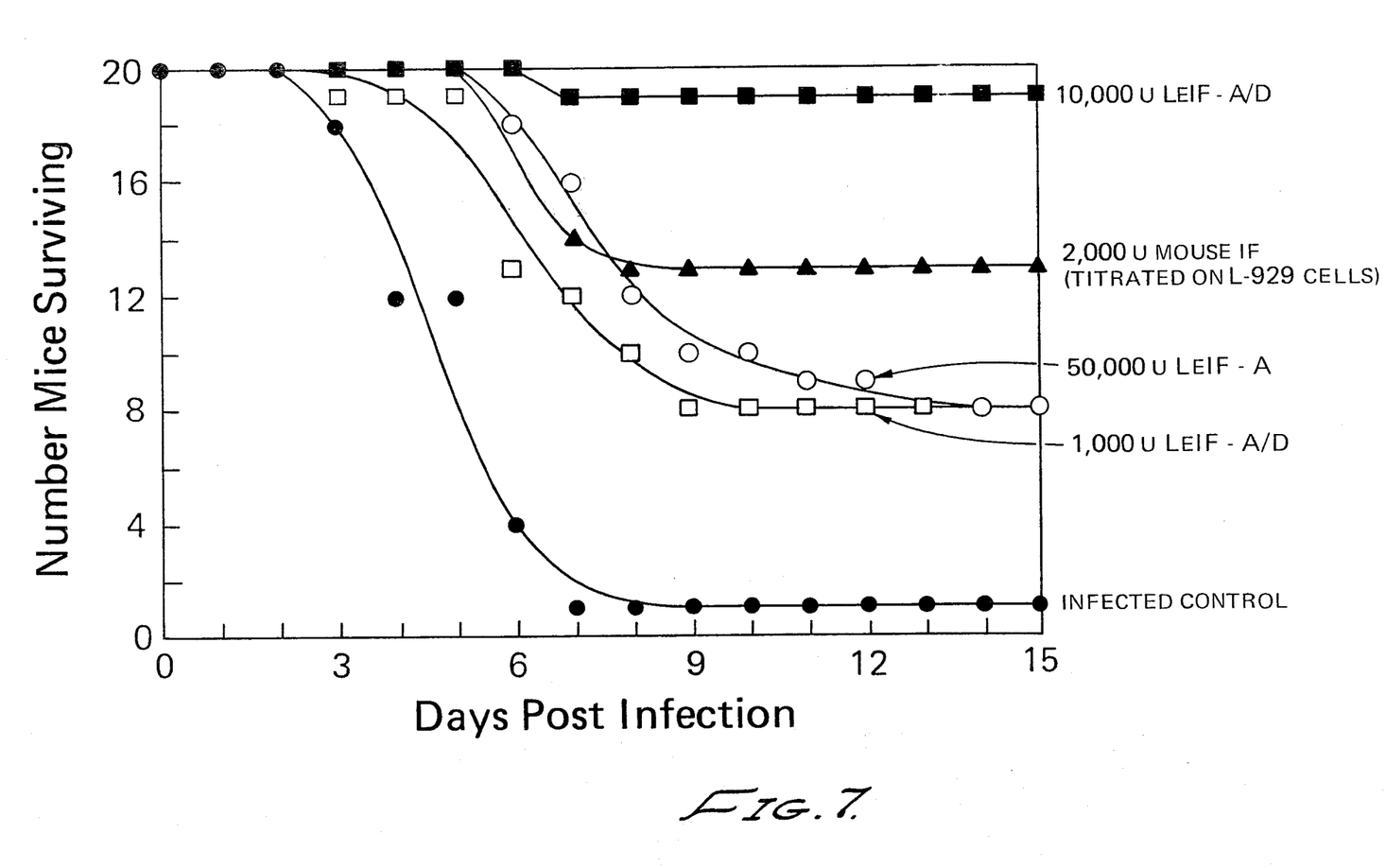
FIGS. 7 and 8 depict the results of comparative testing involving LeIF-A/D and other interferons against EMC virus infections in, respectively, mice and hamsters. The data in FIG. 7 result from treatments i.p. 3 hrs. before infection. Dosages of LeIF-A/D and LeIF-A are as titrated on WISH cells.

The activity of LeIF-A/D against other viruses was also examined. The data in FIG. 5 show antiviral effects against EMC virus infection of L-cells and the data in FIG. 6 shows effects against VSV infection of L-cells. It is clear from these data that the greater activity of LeIF-A/D is not confined to one virus (VSV) and its greater activity is likely to be a general property against many viruses. Natural human buffy-coat interferon preparations have no effect against mouse cells (see Table 2). The activity of LeIF-A/D against EMC virus infection of CD-1 mice was therefore examined. The results in FIG. 7 show that LeIF-A/D is extremely potent against lethal EMC virus infection and LeIF-A also has antiviral activity, as is to be expected from the activity in cell lines (Table 2). The data in FIG. 7 result from treatments i.p. 3 hrs. before infection. Dosages of LeIF-A/D and LeIF-A are as titrated on WISH.

Figure 8:
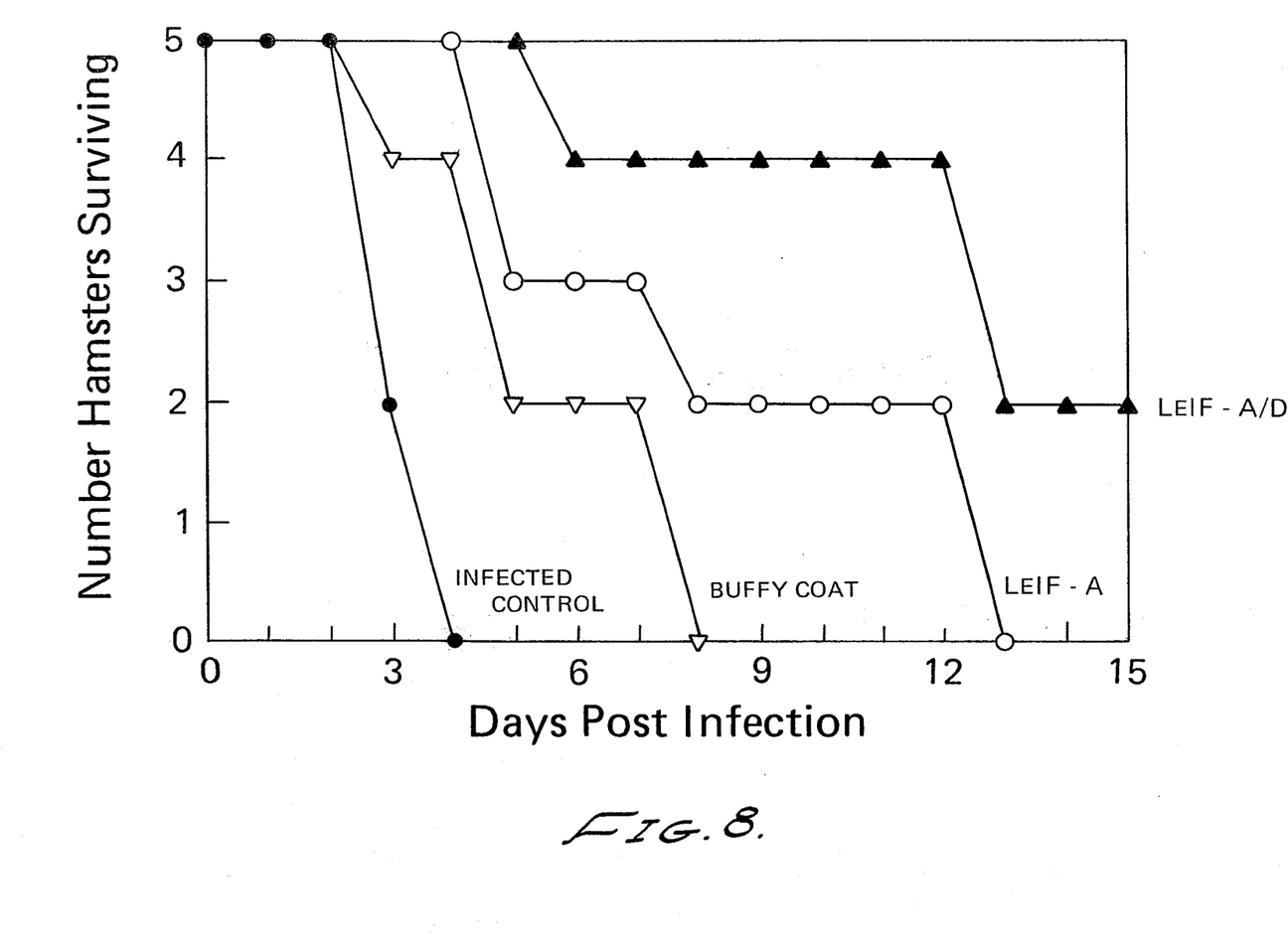

Lethal EMC virus infection of hamsters is also affected by LeIF-A/D and LeIF-A (FIG. 8), the former being the most effective, and buffy coat interferon shows only a small and statistically insignificant effect. In the case of FIG. 8, all interferons were given i.p. 3 hrs. before infection at a dose of $5 \times 10^5$ µ/kg, titrated on WISH cells.

These results indicate that the pronounced antiviral effects of LeIF-A/D in a range of mammalian species is not confined to cell cultures but is also observed in lethal virus infections.

EMC virus can be considered a model system, a demonstration of antiviral effect against which may be predictive of antiviral effect against the represented family of viruses, e.g., the picornavirus family of which foot and mouth disease and polio are members. VSV virus can be considered a model system, a demonstration of antiviral effect against which may be predictive of antiviral effect against the represented family of viruses, e.g., the rhabdovirus family of which rabies is the most important member.

Table 4 tabulates the activities of various of the LeIF hybrids hereof on WISH and MDBK cells and the activity ratios thereof:

TABLE 4

| LeIF Hybrid (PvuII) | Units/liter culture WISH Cells | Units/liter culture MDBK Cells | Ratio Activities WISH/MDBK |
|---|---|---|---|
| AB | $2.4 \times 10^8$ | $4 \times 10^7$ | 6 |
| AD | $1.2 \times 10^8$ | $2 \times 10^7$ | 6 |
| AF | $6 \times 10^7$ | $1 \times 10^7$ | 6 |
| AG | $4 \times 10^7$ | $1.5 \times 10^7$ | 2.7 |

TABLE 4-continued

| LeIF Hybrid (PvuII) | Units/liter culture WISH Cells | Units/liter culture MDBK Cells | Ratio Activities WISH/MDBK |
|---|---|---|---|
| BA | $1.5 \times 10^7$ | $1 \times 10^7$ | 1.5 |
| BD | $6 \times 10^7$ | $1.5 \times 10^7$ | 4 |
| BF | $1 \times 10^6$ | $3.5 \times 10^5$ | 0.3 |
| BG | $2 \times 10^7$ | $6 \times 10^7$ | 0.3 |
| DA | $3 \times 10^6$ | $1.2 \times 10^8$ | 0.025 |
| DB | $2 \times 10^6$ | $5 \times 10^7$ | 0.04 |
| DF | $2 \times 10^5$ | $4 \times 10^6$ | 0.05 |
| DG | $2 \times 10^5$ | $1.5 \times 10^7$ | 0.014 |
| FA | $2 \times 10^5$ | $6 \times 10^7$ | 0.003 |
| FB | $2 \times 10^6$ | $8 \times 10^7$ | 0.025 |
| FD | $1 \times 10^7$ | $2 \times 10^7$ | 0.5 |
| FG | $1 \times 10^6$ | $4 \times 10^7$ | 0.025 |
| A* | $8 \times 10^7$ | $1.2 \times 10^8$ | 0.7 |
| B* | $8 \times 10^7$ | $4 \times 10^8$ | 0.2 |
| C* | $2 \times 10^7$ | $1.5 \times 10^7$ | 1.3 |
| D* | $5 \times 10^6$ | $2.5 \times 10^7$ | 0.2 |
| F* | $2 \times 10^7$ | $2 \times 10^8$ | 0.1 |

*For comparison purposes

APPENDIX A

THE STRUCTURE OF EIGHT DISTINCT CLONED HUMAN LEUKOCYTE INTERFERON cDNAs

David V. Goeddel, David W. Leung, Thomas J. Dull, Mitchell Gross, Richard M. Lawn, Russell McCandliss*, Peter H. Seeburg, Axel Ullrich, Elizabeth Yelverton, and Patrick W. Gray Department of Molecular Biology, Genentech, Inc., 460 Pt. San Bruno Blvd., South San Francisco, California 94080

*Roche Institute of Molecular Biology, Nutley, New Jersey 07110

The interferons are a family of proteins which confer viral resistance in target cells (1,2) as well as inhibiting cell proliferation and modulating immune response (see refs. 2, 3 for reviews). Human interferons were originally classified by their respective cells of origin. The major interferons produced in leukocytes (LeIF or IFN-α) and in fibroblasts (FIF or IFN-β) have been shown to be antigenically distinct, acid-stable molecules collectively designated "classical" or type I interferons. Intense clinical interest in interferon coupled with the inability to obtain large amounts of the purified protein from human cells has spurred efforts to produce high yields of human interferon in the bacterium E. coli via recombinant DNA procedures. Several groups have recently reported the bacterial synthesis of various interferons (4-9) and, in one instance, the efficacy of such material in limited animal testing has been demonstrated (5).

We recently described the construction of a collection of cDNA clones prepared using 12S RNA isolated from a human myeloblastoid cell line (5). Several cDNA clones were identified by hybridization with synthetic DNA probes designed from partial amino acid sequence information of human leukocyte interferon. The cDNA insert of one of the hybrid plasmids (pL31) was sequenced and used to construct a plasmid which directed the synthesis of large amounts of a biologically active human LeIF, termed LeIF A (5). Restriction endonuclease analysis showed extensive differences between the additional hybridizing clones, suggesting that several different human LeIFs might be expressed by the myeloblastoid cell line KG-1 (10). Furthermore, pL31 differs considerably from the human LeIF cDNA clone described by Weissmann and colleagues (4) in both nucleotide sequence and deduced amino acid sequence; yet both of the encoded LeIFs display antiviral activity (4,5).

Additional evidence for the existence of a multigene family of human LeIFs is found in the heterogeneity of the IF proteins prepared from human leukocytes (11) and lymphoblasts (12,13). NH$_2$-terminal amino acid sequences (12-14) and amino acid sequences of tryptic and chymotryptic peptides (13) have revealed at least five distinct, but homologous, LeIFs. At least eight distinct chromosomal LeIF genes have recently been isolated from a human gene library (15; R.L. and A.U., unpublished results). In contrast, there is at present no evidence for multiple human FIF genes. NH$_2$-terminal amino acid sequences of FIF determined by two different groups (16,17) are in agreement with results obtained from nucleotide sequencing of cloned FIF cDNAs (7,18,19) and FIF mRNA (20,21) in suggesting that there may be only one gene for FIF. We describe here genomic hybridization data consistent with the existence of approximately ten human LeIF genes and a single FIF gene, and present the DNA sequences of eight distinct LeIF cDNA clones identified in a cDNA library prepared from the myeloblastoid cell line KG-1.

Evidence for Multiple LeIF Genes

To estimate the number of LeIF genes in the human genome, human spleen DNA was digested with various restriction endonucleases, electrophoresed through agarose gels and transferred to nitrocellulose paper (22). Hybridizations were performed with radiolabelled LeIF and FIF (7) cloned cDNAs.

Identification and Classification of Multiple LeIF cDNA Clones

To investigate the multiplicity of cloned human LeIF cDNAs an in situ colony screening procedure (23) was performed on 4,000 individual colonies of our cDNA library. Approximately 50 clones hybridized to a 260 base pair BglII fragment from pL31 encoding amino acids 61 through 150 of LeIF A. 33 of the 50 contained cDNA inserts of 700 base pairs or longer and were selected for further analysis. The cDNA inserts were mapped using the restriction enzymes PvuII, BglII, and EcoRI, since PvuII and BglII had been found to cleave LeIF A cDNA (5) and all three cut the LeIF cDNA cloned by Nagata et al. (4). The restriction endonuclease maps thus obtained permitted us to divide the LeIF cDNAs into 8 groups The largest cDNA inserts in each group were sequenced by a combination of the Maxam-Gilbert chemical procedure (24) and the dideoxy chain termination procedure using the bacteriophage M13 cloning vector mp7 (25). It remained possible that different LeIF cDNAs would display the same restriction enzyme map. Since the 3'-noncoding regions of the 8 sequenced cDNA clones showed much less homology than their respective coding portions, the 3' regions of several cDNAs in each group were partially sequenced. This analysis revealed that one of the cDNA clones originally classified as type C was actually a LeIF H cDNA clone which did not extend to the single 5' PvuII site. Fourteen of the 33 LeIF cDNA clones analyzed were LeIF A and 9 were LeIF D. No other type of clone was represented more than twice in this collection. This result was not an artifact of the use of LeIF A cDNA as the original hybridization probe. No additional LeIF cDNA clones were found when the 4,000 colonies of the cDNA library were re-tested using mixed LeIF A, B, C, E and F cDNA probes.

LeIF D has the same restriction pattern as the LeIF cDNA clone described by Nagata et al. (4). The only difference between the two clones in predicted amino acid sequence is at position 114 where valine is found in LeIF D instead of an alanine (26). Weissmann and co-workers (6) have also recently sequenced a partial length LeIF cDNA clone of a second type (which they named $\alpha_2$) differing from LeIF A only at the codon for amino acid 23 (arginine for $\alpha_2$ vs. lysine for LeIF A).

A LeIF Pseudogene is Transcribed

Figure 4:
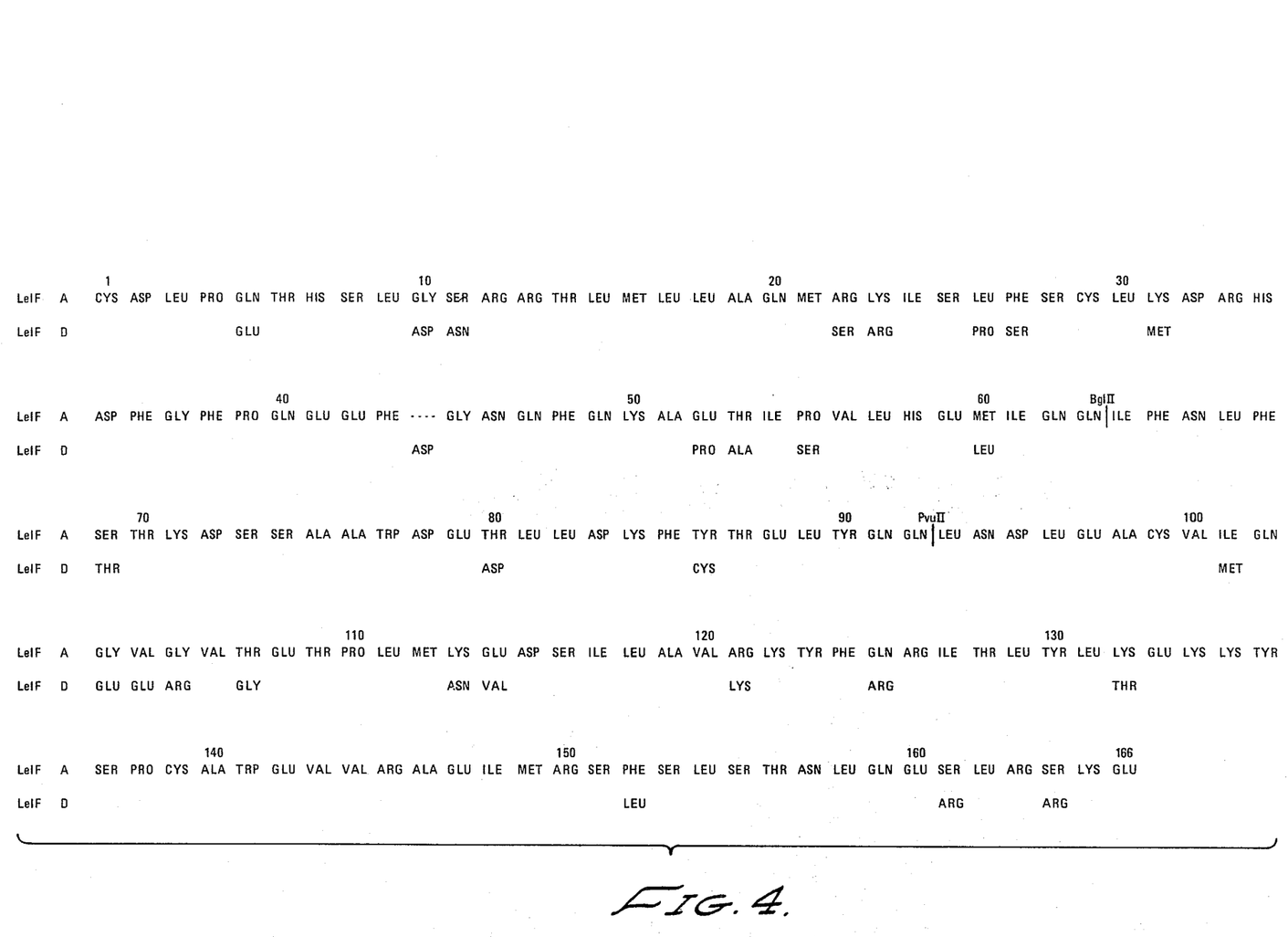
FIG. 4 compares the amino acid sequence of mature leukocyte interferons A and D, a deletion of amino acid 44 in LeIF A being indicated by dashes. Only those LeIF D amino acids which differ from corresponding amino acids of LeIF A are depicted: the amino acid sequence of LeIF D is otherwise identicial of LeIF A.

The coding region of the LeIF E cDNA clone contains one nucleotide more than the other LeIF cDNAs. The predicted amino acid sequence from this nucleotide insertion onwards (amino acid residue 40 in LeIF E) bears no resemblance to the other LeIF protein sequences and results in several in-phase termination codons, the first of which would appear at amino acid position 60. Therefore, the amino acid sequence is presented in FIG. 4 as if this insertion had not occurred. Even with this adjustment, termination codons are encountered at positions 102 and 155. Hence, termination codons occur in all three reading frames. The fact that a cDNA was cloned which contains an additional nucleotide in the coding sequence for a LeIF may reflect an artifact created somewhere during the process of reverse transcription of mRNA and sequence amplification in E. coli. However, the presence of the two additional termination codons could imply that LeIF E is a copy of a pseudogene analagous to the $\alpha$- and $\beta$-globin pseudogenes (27-29). If so, this is the first reported evidence of a pseudogene being transcribed into RNA. The biological significance of the transcription and possible translation of this pseudogene has not been determined. The fact that only one cDNA clone of a LeIF pseudogene was obtained in our extensive search for LeIF cDNA clones suggests that the transcription of such genes may be very rare. This observation is further supported by our recent isolation from a human chromosomal DNA library of an additional LeIF pseudogene having a DNA sequence distinct from the eight LeIF cDNA clones described here (unpublished results).

LeIF Signal Peptides

The signal sequences of human LeIFs A, B, C, D, F and H possess features common to all eukaryotic secretory protein signal sequences. Each contains a long stretch of hydrophobic amino acids residues, perhaps important for association with and traversal of the rough endoplasmic reticulum membrane. The hydrophobic regions are flanked by charged and more polar amino acid residues. The signal sequences are rich in serine residues proximal to the prepeptide cleavage site, analogous to the signal sequences of rat proalbumin (30) and certain mouse immunoglobin chains (31). Within the cell, removal of the signal peptides is presumably achieved by peptide cleavage between glycine and cysteine residues in all of these LeIFs.

The signal sequences of many different proteins have been determined and compared (32). No major sequence homologies have been detected; the most general feature may be structural in nature (see ref. 33 for review). It is possible that the junction of distinct structural domains within the signal peptide is recognized by a processing enzyme or signal peptidase (34), resulting in production of the mature secreted protein and complete translocation into the lumen of the rough endoplasmic reticulum.

The signal sequences of the LeIFs reported here are only about 70 percent homologous when compared with each other, except for types C and F which are identical (Table 1). Only 11 of the 23 amino acids (43 percent) occur in invariant positions in all six prepeptides. The sequence of the human fibroblast interferon signal peptide (7,18-20) is completely different from those of the human LeIFs.

Mature Leukocyte Interferons

The mature LeIFs are more closely related in their amino acid sequences (approximately 80 percent homology) than are their corresponding signal peptides (See Table 1). A total of 79 out of 166 amino acids (48 percent) of the mature polypeptide are identical in all sequences examined. If the LeIF E pseudogene amino acid sequence is ignored then 99 amino acids (60 percent) occupy identical positions. When the human FIF sequence (7,18,19,21) is compared with the LeIF sequences, only 39 amino acids out of 166 (23 percent) appear in identical positions. The overall distribution of amino acid differences along the LeIF molecules appears to be random with the possible exception of the region between amino acids 115 and 151. All the LeIF cDNA clones (again excluding LeIF E) code for the same amino acid in 31 out of 37 (84 percent) positions in this region. Residues 116 to 150 also display the greatest similarity to FIF (17 out of 35 positions identical), suggesting that this region is of functional importance.

The changes in amino acid sequences between the LeIFs are largely due to single nucleotide changes; there are several sites (i.e. positions 37, 107, 160) where nonconservative amino acid changes occur. It is interesting to note that the nucleotide sequence of LeIF B contains an insertion of a thymidine residue after nucleotide 362 (codon 98). This insertion changes the translational reading frame and results in four distinct codon changes. Then after position 373 (codon 101) an adenosine residue has been deleted which restores the original reading frame:

| | 97 | | | | | 102 |
|---|---|---|---|---|---|---|
| LeIF A | glu | ala | cys | val | ile | gln |
| | GAA | GCC | TGT | GTG | ATA | CAG |
| LeIF B | glu | val | leu | cys | asp | gln |
| | GAA | GTC | CTG | TGT | GAT | CAG |

The shorter (~800 base pairs) of the two LeIF H type cDNA clones, which we have designated LeIF $H_1$, has a deletion (cytidine, nucleotide number 545) which is followed 6 nucleotides later by a correcting insertion (guanosine, after position 551):

| | 158 | | | | 162 |
|---|---|---|---|---|---|
| LeIF H | leu | gln | lys | arg | leu |
| | TTG | CAA | AAA | AGA | TTA |
| LeIF $H_1$ | leu | lys | lys | gly | leu |
| | TTG | AAA | AAA | GGA | TTA |

Except for this difference and a single base change in the 3' noncoding regions, the nucleotide sequences of LeIF H and LeIF $H_1$ cDNAs are identical. It is possible these two cDNA clones may represent allelic forms of a single LeIF gene found in the KG-1 cell line.

The location of cysteine residues is often highly conserved in proteins. All the LeIFs which we have sequenced code for cysteines at positions 1 and 139 of the mature protein. All predicted LeIFs except LeIF E contain a cysteine at position 29; all except LeIF B (Cys-100) contain a cysteine at position 99. At least one intramolecular disulfide bridge has been predicted on the basis of loss of interferon activity upon incubation with reducing agents (35). Allen and Fantes (13) have shown that the N-terminal cysteine is probably involved in a disulfide bond. Furthermore, the presence of two disulfide bridges in the LeIF A produced in *E. coli* (5) has been established by analysis of tryptic digests of the purified protein: Cys-1 is bonded to Cys-99 and Cys-29 is bonded to Cys-139 (R. Wetzel, personal communication). The fact that cysteine residues are also predicted in human FIF (7,18,19,21) in the positions corresponding to amino acids 29 and 139 of LeIF suggests that this disulfide bond also occurs in FIF.

$NH_2$-terminal sequences of human LeIF species isolated from lymphoblasts (12,13) and leukocytes (14) have been determined by protein microsequence analysis. The sequences determined by Zoon et al. (12) and Levy et al. (14) both have $NH_2$-terminal serine residues. The sequences published by Allen and Fantes (13) begin with cysteine residues. The seven full length LeIF cDNAs (A-F, H) all code for mature LeIFs beginning with cysteine. While it is possible that a LeIF cDNA clone will be identified which encodes an N-terminal serine, it is more likely that the determination of serine arose by artifactual oxidation of cysteine during the initial protein microsequencing procedure.

Disregarding the discrepancies at amino acid position one, the following comparisons can be made. The 32 $NH_2$-terminal amino acids of the lymphoblastoid IF sequence of Zoon et al. (12) have the greatest homology with LeIF F, with only position 26 (Pro in LeIF F, Leu in lymphoblastoid IF) differing between the two species. The 22 $NH_2$-terminal amino acids of LeIF determined by Levy et al. (14) show the most homology with LeIF A. These two LeIFs differ only at position 11 (Asn in the Levy sequence vs. Ser for LeIF A). Allen and Fantes have determined the sequences of tryptic and chymotryptic peptides of two forms of LeIF, IFN-αA and IFN-αB (13). IFN-αA consists of at least two different polypeptides of 165 amino acids having the same amino acid deletion at position 44 that is predicted by the LeIF A cDNA sequence. 140 of the 142 amino acids which have been determined from the IFN-αA peptides correspond to the LeIF A cDNA sequence presented here. Only Asp-84 and Pro-88 of IFN-αA are not predicted by the LeIF A cDNA sequence. IFN-αB consists of at least three polypeptides of 166 amino acids each and the residues present at 161 positions have been determined (13). Peptides of IFN-αB are most closely related to LeIF D, with only Met-60, Thr-64, and Ala-114 not being predicted by the LeIF D cDNA sequence. The 77 N-terminal amino acids of LeIF F are found in the IFN-αB peptide sequences. However, there are eleven differences between these two interferon sequences in the C-terminal portion (residues 78-166) of the polypeptides. Amino acid sequences deduced from LeIF B, C, G and H cDNAs do not appear to be represented in either IFN-αA or IFN-αB peptide sequences. These comparisons seem to suggest the presence of additional LeIF genes, cDNA copies of which are not present, or have not been identified, in our cDNA library. Whether some of the slight differences among LeIF sequences described above could be due to allelic variation in the human population awaits a detailed genomic characterization of the LeIF gene family from an individual.

Noncoding Sequences of LeIF

A limited amount of sequence information is available for the 5' noncoding regions of the LeIF cDNAs. Obvious homologies exist in the regions immediately preceding the translational initiation codon; LeIFs A, B and D are similar in this region, as are LeIFs C and F.

The 3' noncoding regions of the LeIF cDNA clones vary in size from 242 (LeIF D) to 441 (LeIF B) base pairs, counting from the first nucleotide of the stop codon to the site of polyadenylation. The overall homology between 3' noncoding regions is lower than that within the protein coding regions, although certain portions of the 3' noncoding region are relatively conserved. Both the reduced level of 3' noncoding homology and the substantial deletions in the sequence alignments resemble the situation found in comparing the analogous DNA sequences of members of the human β-like globin gene family (36). As those authors point out, such findings suggest that the precise sequence of much of the 3' noncoding regions of eukaryotic mRNAs is not essential for function. Experiments involving in vitro translation of mRNAs with large 3' deletions support this contention (37,38).

Efstratiadis and coworkers (36) have noted that short (2-8 bp) tandem repeats often surround the sites of deletions in the β-like globin gene family 3' noncoding sequences. They suggested a mechanism of "slippage" during DNA replication followed by scission of resulting single stranded DNA loops as a possible cause of these deletion events during evolution. Such short tandem repeats also occur at many of the deletion points in the LeIF cDNA sequences.

The hexanucleotide AATAAA precedes the site of polyadenylation in many eukaryotic cellular mRNAs by 15-25 bases (39). Although exceptions to the rule have been found in several RNA viruses (40), this sequence is thought to be involved in mRNA processing and/or polyadenylation. A variant of this sequence, AATTAAA, has recently been reported which proceeds the poly(A) site in rat amalyase (41) and anglerfish somatostatin (42) mRNAs. LeIF A, D and F cDNAs contain the hexanucleotide AATAAA ending 20, 21 and 14 nucleotides, respectively, from their polyadenylation sites. LeIF B, C, E, G and H cDNAs do not contain this hexanucleotide. At the nucleotide position corresponding to AATAAA in the two shortest mRNAs (A and D), the sequence of the other mRNAs differ by one or two nucleotides. This sequence divergence may have led to the extension of the 3' non-coding region in those genes. While LeIF F mRNA continues until an AATAAA is encountered 14 nucleotides before its poly(A) site, LeIF C, E, G and H possess the related hexanucleotide ATTAAA near their 3' termini (positions 378-383). LeIF B also has the ATTAAA sequence at this position, but is not polyadenylated until another ATTAAA sequence is reached at positions 463-468. It should be noted that the two cDNA clones most often isolated (LeIF A and D) possess the canonical hexanucleotide at the same position and cDNA clones corresponding to the other LeIFs are rare. Therefore, it is conceivable that transcription of the genes for the rarer mRNA species might often continue until a stronger polyadenylation signal is reached, resulting in LeIF mRNA species larger than 12S. However, none of the 10 total rare LeIF cDNA clones (types B, C, E, F and H) we have isolated contain additional 3' noncoding nucleotides.

Significance of the LeIF multigene family

We have presented here the sequences of eight distinct human LeIF cDNAs, seven of which probably code for functional interferon polypeptides. LeIF amino acid sequence information (12-14) suggests the presence of yet additional LeIF structural genes. Genomic blots and the isolation of chromosomal LeIF sequences (15) also support the concept of a LeIF multigene family consisting of at least 8-10 distinct human LeIF-related genes, although some of these could be pseudogenes similar to LeIF E.

The cDNA clones LeIF A and LeIF D occur relatively frequently in our cDNA library (5) which was prepared using RNA from the virus-induced myeloblastoid cell line KG-1 (10). In contrast, a major LeIF species found in the lymphoblastoid Namalwa cell line (12) most closely resembles the polypeptide encoded by LeIF F cDNA. This finding supports the suggestion of Nagata et al. (15) that different cell types might preferentially express different LeIF genes. Preferential expression of different interferons might also occur in the same cell line in response to different viruses.

These multiple LeIFs probably exhibit distinct functional properties. Streuli et al. (6) have shown that two different LeIFs (IFN-α1 and IFN-α2) have striking differences in their antiviral activities on cells of different species. We have recently obtained expression in *E. coli* of the mature LeIF polypeptides encoded by LeIF A, B, C, D, and F cDNAs (unpublished results). All five of these interferons exhibit different cross-species specificities. The availability of these cloned LeIFs should permit the assignment of the various activities characteristic of mixed leukocyte interferon preparations (2) to individual LeIF species. A detailed understanding of the correlation between LeIF structure and activity may lead to the design of new interferons highly active against particular diseases.

REFERENCES

1. Isaacs, A. and Lindenmann, J. *Proc. R. Soc. B147*, 258-267 (1957).
2. Stewart, W. E. II *The Interferon System*, Springer, New York (1979).
3. Baron, S. and Dianzani, F. (eds.) *Tex. Rep. Biol. Med.* 35, 1-573 (1977).
4. Nagata, S., Taira, H., Hall, A., Johnsrud, L., Streuli, M., Escodi, J., Boll, W., Cantell, K. and Weissmann, C. *Nature* 284, 316-320 (1980).
5. Goeddel, D. V., Yelverton, E., Ullrich, A., Heyneker, H. L., Mirozzari, G., Holmes, W., Seeburg, P. H., Dull, T., May, L., Stebbing, N., Crea, R., Maeda, S., McCandliss, R., Sloma, A., Tabor, J. M., Gross, M., Familletti, P. C. and Pestka, S. *Nature* 287, 411-416 (1980).
6. Streuli, M., Nagata, S. and Weissmann, C. *Science* 209, 1343-1347 (1980).
7. Goeddel, D. V., Shepard, H. M., Yelverton, E., Leung, D., Crea, R., Sloma, A. and Pestka, S. *Nucleic Acids Res.* 8, 4057-4074 (1980).
8. Derynck, R., Remaut, E., Saman, E., Stanssens, P., DeClercq, E., Content, J. and Fiers, W. *Nature* 287, 193-197 (1980).
9. Taniguchi, T., Guarante, L., Roberts, T. M., Kimelman, D., Douhan, J. and Ptashne, M. *Proc. Natn. Acad. Sci. U.S.A.*, 5230-5233 (1980).
10. Koeffler, H. P. and Golde, D. W. *Science* 200, 1153-1154 (1978).
11. Rubinstein, M., Rubinstein, S., Familleti, P. C., Miller, R. S., Waldman, A. A. and Pestka, S. *Proc. Natn. Acad. Sci. U.S.A.* 76, 640-644 (1979).
12. Zoon, K. C., Smith, M. E., Bridgen, P. J., Anfinsen, C. B., Hunkapillar, M. W. and Hood, L. E. *Science* 207, 527-528 (1980).
13. Allen, G. and Fantes, K. H. *Nature* 287, 408-411 (1980).
14. Levy, W. P., Shively, J., Rubinstein, M., Del Valle, U. and Pestka, S. *Proc. Natn. Acad. Sci. U.S.A.* 77, 5102-5104 (1980).
15. Nagata, S., Mantei, N. and Weissmann, C. *Nature* 287, 401-408 (1980).
16. Knight, E., Jr., Hunkapillar, M. W., Korant, B. D., Hardy, R. W. F. and Hood, L. E. *Science* 207, 525-526 (1980).
17. Stein, S., Kenny, C., Friesen, H-J., Shively, J., Del Valle, U. and Pestka, S. *Proc. Natn. Acad. Sci. U.S.A.* (in the press).
18. Taniguchi, T., Ohno, S., Fujii-Kuriyama and Muramatsu, M. *Gene* 10, 11-15 (1980).
19. Derynck, R., Content, J., DeClercq, E., Volckaert, G., Tavernier, J., Devos, R. and Fiers, W. *Nature* 285, 542-547 (1980).
20. Houghton, M., Stewart, A. G., Doel, S. M., Emtage, J. S., Eaton, M. A. W., Smith, J. C., Patel, T. P., Lewis, H. M., Porter, A. G., Birch, J. R., Cartwright, T. and Carey, N. H. *Nucleic Acids Res.* 8, 1913-1931 (1980).
21. Houghton, M., Eaton, M. A. W., Stewart, A. G., Smith, J. C., Doel, S. M., Catlin, G. H., Lewis, H. M., Patel, T. P., Emtage, J. S., Carey, N. H. and Porter, A. G. *Nucleic Acids Res.* 8, 2885-2894.
22. Southern, E. M. *J. Molec. Biol.* 98, 503-517 (1975).
23. Grunstein, M. and Hogness, D. S., *Proc. Natn. Acad. Sci. U.S.A.* 72, 3961-3965 (1975).
24. Maxam, A. M. and Gilbert, W. *Methods Enzymol.* 65, 499-560 (1980).
25. Messing, J., Crea, R. and Seeburg, P. H. *Proc. Natn. Acad. Sci. U.S.A.* (in the press).
26. Mantei, N., Schwarzstein, M., Streuli, M., Panem, S., Nagata, S. and Weissmann, C. *Gene* 10, 1-10 (1980).
27. Fritsch, E. F., Lawn, R. M. and Maniatis, T. *Cell* 19, 959-972 (1980).
28. Proudfoot, N. J. and Maniatis, T. *Cell* 21, 537-544 (1980).
29. Proudfoot, N. J., Shander, M. H. M., Manley, J. L., Gefter, M. L. and Maniatis, T. *Science* 209, 1329-1336 (1980).
30. Strauss, A. W., Bennett, C. D., Donohue, A. M., Rodkey, J. A. and Alberts, A. W. *J. Biol. Chem.* 252, 6846-6855 (1977).
31. Burnstein, Y., Zemell, R., Cantor, F. and Schechter, I. *Proc. Natn. Acad. Sci. U.S.A.* 74, 3157-3161 (1977).
32. Hebner, J. F., Rosenblatt, M., Kemper, B., Kronenberg, H. M., Rich, A. and Potts, J. T. *Proc. Natn. Acad. Sci. U.S.A.* 75, 2616-2620 (1978).
33. Blobel, G., Walter, P., Cheng, C. N., Goldman, D., Erickson, A. H. and Lingappa, V. R. *Symp. Soc. Experimental Med.* 33, 9-36 (1979).

34. Jackson, R. C. and Blobel, G. *Proc. Natn. Acad. Sci. U.S.A.* 74, 5598–5602 (1977).
35. Morgensen, K. E. and Cantell, K. *J. Gen. Virol.* 22, 95–103 (1974).
36. Efstratiadis, A., Posakony, J. W., Maniatis, T., Lawn, R. M., O'Connell, C., Sprtiz, R. A., De Riel, J. K., Forget, B., Weissman, S. M., Slighton, J. L., Blechl, A. E., Smithies, O., Baralle, F. E., Shoulders, C. C. and Proudfoot, N. J. *Cell* (in the press).
37. Kronenberg, H. M., Roberts, B. E. and Efstratiadis, A. *NucleicAcids Res.* 6, 153–166 (1979).
38. Nunberg, J. H., Kaufman, R. J., Chang, A. C. Y., Cohen, S. N. and Schimke, R. T. *Cell* 19, 355–364 (1980).
39. Proudfoot, N. J. and Brownlee, G. G. *Nature* 263, 211–214 (1976).
40. Porter, A. G., Fellner, P., Black, D. N., Rowlands, D. J., Harris, T. J. R. and Brown, F. *Nature* 276, 298–301 (1978).
41. MacDonald, R. J., Crerar, M. M., Swain, W. F., Pictet, R. L., Gilles, T. and Rutter, W. J. *Nature* 287, 117–122 (1980).
42. Hobart, P., Crawford, R., Shen, L. P., Pictet, R. and Rutter, W. J. *Nature* (in the press).
43. Blin, N. and Stafford, D. W. *Nucleic Acids Res.* 3, 2303–2308 (1976).
44. Taylor, J. M., Illemensee, R. and Summer, S. *Biochem. Biophys. Acta* 442, 324–330 (1976).
45. Denhardt, D. T. *Biochem. Biophys. Res. Commun.* 23, 461–467 (1966).
46. Dayoff, M. O. *Atlas of Protein Sequence and Structure 5*, Suppl. 3, Natn. Biomedical Res. Foundation, Washington, D.C. (1978).

TABLE 1

Pairwise comparisons of differences in coding sequences of human LeIFs

|   | A | B | C | D | E | F | G | H |   |
|---|---|---|---|---|---|---|---|---|---|
| A |   | 31(19) | 31(19) | 29(17) | 41(25) | 30(18) | 18*(14) | 28(17) |   |
| B | 7(30) |   | 32(19) | 38(23) | 45(27) | 31(19) | 23*(17) | 29(17) |   |
| C | 7(30) | 8(35) |   | 32(19) | 41(25) | 18(11) | 21*(16) | 23(14) | Ma- |
| D | 6(26) | 9(39) | 8(35) |   | 44(27) | 28(17) | 17*(13) | 32(19) | ture |
| E | — | — | — | — |   | 37(22) | 24*(18) | 42(25) | LeIFs |
| F | 7(30) | 8(35) | 0(0) | 8(35) | — |   | 15*(11) | 28(17) |   |
| G | — | — | — | — | — | — |   | 18*(14) |   |
| H | 6(26) | 6(26) | 6(26) | 4(17) | — | 6(26) | — |   |   |
| LeIF Signal Peptides |

*Only the 133 C-terminal amino acids of LeIF G can be deduced from the cDNA sequence. Therefore, in pairwise comparisons involving LeIF G only differences in these 133 amino acids are considered.

The number of amino acid replacements in each pair of coding sequences are shown. The 23 amino acid signal peptides are compared in the lower left and the 166 amino acid mature LeIFs are compared in the upper right of the Table. The table lists first the total number of differences between pairs, followed by the percentage difference (numbers in parentheses). Signal sequences for LeIF E and LeIF G are not known, so no entries appear for comparisons involving either of these sequences.

What is claimed is:

1. An antiviral composition of matter comprising a polypeptide of 165–166 amino acids, optionally having an additional methionine attached to the ordinarily first amino acid at the N-terminus, the amino acid sequence of said polypeptide comprising, in sequence, discrete sub-sequences corresponding in amino acid identity and number to sub-sequences of different, naturally occurring leukocyte interferons, the amino acid sequence of said polypeptide differing from the amino acid sequence of naturally occurring leukocyte interferons.

2. An antiviral composition of matter according to claim 1 comprising a polypeptide of 166 amino acids, the N-terminal portion of said polypeptide consisting essentially of amino acids 1–92 of LeIF-D and the carboxy terminal portion of said polypeptide consisting essentially of amino acids 92–165 of LeIF-A, the carboxy terminus of said polypeptide corresponding essentially to the carboxy terminus of LeIF A.

3. An antiviral composition of matter according to claim 1 comprising a polypeptide of 165 amino acids, the N-terminal portion of said polypeptide consisting essentially of amino acids 1–91 of LeIF A and the carboxy terminal portion of said polypeptide consisting essentially of amino acids 93–166 of LeIF-D, the carboxy terminus of said polypeptide corresponding essentially to the carboxy terminus of LeIF D.

4. An antiviral composition of matter according to claim 1 comprising a polypeptide of 166 amino acids, the N-terminal portion of said polypeptide consisting essentially of amino acids 1–63 of LeIF D and the carboxy terminal portion of said polypeptide consisting essentially of amino acids 63–165 of LeIF A, the carboxy terminus of said polypeptide corresponding essentially to the carboxy terminus of LeIF A.

5. An antiviral composition of matter according to claim 1 comprising a polypeptide of 165 amino acids, the N-terminal portion of said polypeptide consisting essentially of amino acids 1–62 of LeIF A, the carboxy terminal portion of said polypeptide consisting essentially of amino acids 64–166 of LeIF D, the carboxy terminus of said polypeptide corresponding essentially to the carboxy terminus of LeIF D.

6. An antiviral composition of matter according to claim 1 comprising a polypeptide of 165 amino acids, the N-terminal portion of said polypeptide consisting essentially of amino acids 1–91 of LeIF A and the carboxy terminal portion of said polypeptide consisting essentially of amino acids 93–166 of LeIF B, the carboxy terminus of said polypeptide corresponding essentially to the carboxy terminus of LeIF B.

7. An antiviral composition of matter according to claim 1 comprising a polypeptide of 165 amino acids, the N-terminal portion of said polypeptide consisting essentially of amino acids 1–91 of LeIF A, the carboxy terminal portion of said polypeptide consisting essentially of amino acids 93–166 of LeIF F, the carboxy terminus of said polypeptide corresponding essentially to the carboxy terminus of LeIF F.

* * * * *